US009993641B2

(12) United States Patent
Williams et al.

(10) Patent No.: US 9,993,641 B2
(45) Date of Patent: Jun. 12, 2018

(54) TONGUE STIMULATION FOR COMMUNICATION OF INFORMATION TO A USER

(71) Applicant: Colorado State University Research Foundation, Fort Collins, CO (US)

(72) Inventors: John D. Williams, Fort Collins, CO (US); Joel A. Moritz, Fort Collins, CO (US); Leslie M. Stone-Roy, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days. days.

(21) Appl. No.: 15/583,572

(22) Filed: May 1, 2017

(65) Prior Publication Data

US 2017/0232252 A1    Aug. 17, 2017

Related U.S. Application Data

(63) Continuation-in-part of application No. 14/677,687, filed on Apr. 2, 2015, now Pat. No. 9,669,159.
(Continued)

(51) Int. Cl.
*A61N 1/36*      (2006.01)
*A61N 1/05*      (2006.01)
(Continued)

(52) U.S. Cl.
CPC ............ *A61N 1/0548* (2013.01); *A61F 7/007* (2013.01); *A61F 7/12* (2013.01); *A61M 5/14248* (2013.01);
(Continued)

(58) Field of Classification Search
CPC .............. A61N 1/0548; A61N 1/36014; A61N 1/36128; A61N 1/36057; A61B 5/682; A61M 2210/0643; A61F 2007/0017
See application file for complete search history.

(56) References Cited

U.S. PATENT DOCUMENTS

| 8,874,220 | B2 * | 10/2014 | Draghici | .............. A61N 1/0548 |
| | | | | 607/115 |
| 9,669,159 | B2 | 6/2017 | Williams et al. | |
| 2015/0283384 | A1 * | 10/2015 | Williams | ................ A61F 7/007 |
| | | | | 607/3 |

OTHER PUBLICATIONS

Boliek CA, Rieger JM, Li SYY, Mohamed Z, Kickham J, Amundsen K. Establishing a reliable protocol to measure tongue sensation. *Journal of Oral Rehabilitation*. 2007;34:433-441.
(Continued)

*Primary Examiner* — George Evanisko
(74) *Attorney, Agent, or Firm* — Polsinelli PC

(57) ABSTRACT

Example devices and methods of tongue stimulation for communication of information to a user are disclosed herein. In an example, a tongue stimulation device may include a body configured to be placed entirely within a mouth of the user and atop the tongue of the user. An array of electro-tactile elements may be distributed on the body, wherein each of the electro-tactile elements is configured to stimulate an area of the tongue adjacent the electro-tactile element. A wireless receiver coupled to the body may be configured to receive stimulation information wirelessly from outside the mouth of the user. At least one processing unit coupled to the body may be configured to transform the received stimulation information into a stimulation signal for each of the electro-tactile elements, and to provide the stimulation signals to the electro-tactile elements.

12 Claims, 21 Drawing Sheets

Related U.S. Application Data

(60) Provisional application No. 61/974,866, filed on Apr. 3, 2014.

(51) Int. Cl.
*A61F 7/00* (2006.01)
*A61F 7/12* (2006.01)
*A61M 37/00* (2006.01)
*A61M 5/142* (2006.01)
*A61F 7/02* (2006.01)

(52) U.S. Cl.
CPC ......... *A61M 37/00* (2013.01); *A61N 1/36014* (2013.01); *A61N 1/36057* (2013.01); *A61N 1/36128* (2013.01); *A61F 2007/0017* (2013.01); *A61F 2007/0071* (2013.01); *A61F 2007/0075* (2013.01); *A61F 2007/0295* (2013.01); *A61M 2210/0643* (2013.01)

(56) References Cited

OTHER PUBLICATIONS

Maeyama TM, Plattig KH. Minimal Two-Point Discrimination in Human Tongue and Palate. *Am J Otolaryngol.* 1989;10:342-344.
Moritz Jr. J, Turk P, Williams JD, Stone-Roy LM. Perceived Intensity and Discrimination Ability for Lingual Electrotactile Stimulation Depends on Location and orientation of Electrodes. *Frontiers in Human Neuroscience.* Apr. 21, 2017;11:Article 186.
Novich SD, Eagleman DM. Using space and time to encode vibrotactile information: toward an estimate of the skin's achievable throughput. *Exp Brain Res.* 2015;233:2777-2788.
Non-Final Office Action, U.S. Appl. No. 14/677,687, dated Sep. 16, 2016.
Response to Non-Final Office Action, U.S. Appl. No. 14/677,687, dated Dec. 16, 2016.
Notice of Allowance, U.S. Appl. No. 14/677,687, dated Feb. 1, 2017.

* cited by examiner

TONGUE STIMULATION FOR COMMUNICATION OF INFORMATION TO A USER

RELATED APPLICATION

The present application is a continuation-in-part and claims the benefit of priority to U.S. patent application Ser. No. 14/677,687, titled "Tongue Stimulation for Communication of Information to a User", filed Apr. 2, 2015, the contents of which are hereby incorporated herein by reference in its entirety and which claims the benefit of priority to U.S. Provisional Application No. 61/974,866, titled "Device and Method for Electrical and Electrochemical Stimulation of the Tongue," filed Apr. 3, 2014, the contents of which are hereby incorporated herein by reference in its entirety.

FIELD OF THE INVENTION

The present application relates to medical apparatus and methods. More specifically, the present application relates to stimulation of the tongue of a user for communication of information to the user.

BACKGROUND OF THE INVENTION

Persons suffering from the reduction or loss of one or more sensory capabilities (e.g., the sense of sight, hearing, balance, or touch) typically suffer a restriction in the amount and/or quality of sensory information such persons may receive. Such reduction of sensory information may be caused by birth defects, bodily injury, and so on. In some examples, medical devices have been developed to allow a person to regain some level of lost sensory capability in some cases. For example, hearing aids, cochlear implants, and other devices designed to interact with the human ear have served to enhance the hearing capabilities of those suffering from some types or severities of hearing loss. However, such devices do not address all types of hearing loss issues.

To address such issues in other ways, systems have been developed to employ an unimpaired sense of a user to relay information that would ordinarily be received via another sense that is impaired for that particular user. For example, Braille is a tactile writing system that facilitates reading of written materials by the visually impaired. More recently, screen reader software has been developed that interprets information to be presented on a computer screen and presents that information via text-to-speech (TTS) or other audio or tactile output. Closed captioning has long been employed to provide speech and other audio information via text displayed on a television or motion picture screen. Descriptive Video Service® (DVS) is a video description service that provides additional audio information (e.g., speech) descriptive of the visual information being presented in a movie or television program.

Some electronic systems have been designed to provide visual information by way of a tactile input. Such systems are often called "tactile visual substitution systems" (TVSS). Some recent academic research has been focused on employing the human tongue as a conduit through which visual information may be communicated to the user. This type of TVSS is termed a "tongue display unit" (TDU), which may be employed as a type of tactile visual substitution device, includes an array of electrodes configured to apply electro-tactile stimulation in one or more patterns to areas of the dorsal (upper) side of a user's tongue to relay the visual information. The electrodes may be arranged on a medium to be placed in the mouth atop the tongue of the user. The electrodes are connected by multiple wires to a signal generator located outside the body and controlled via a microcontroller so that the signal generator produces stimulation pulses for application to the tongue via the electrodes. Using such systems, the average human tongue may be able to sense about a one order of magnitude difference in electro-tactile stimulation, from a low stimulation level that is just barely perceptible, to a high stimulation level at which the perceived stimulation starts becoming uncomfortably intense.

With the above concepts in mind, as well as others not explicitly discussed herein, various embodiments of systems and methods for tongue stimulation for communication of information to a user are disclosed herein.

SUMMARY

In one embodiment, a tongue stimulation device may include a body to be placed entirely within a mouth of a user and atop the tongue of the user, an array of electro-tactile elements distributed on the body to stimulate corresponding areas of the tongue, a wireless receiver to receive stimulation information wireless from outside the mouth of the user, and at least one processing unit to transform the received stimulation information into a stimulation signal for each of the electro-tactile elements and to provide the stimulation signals to the electro-tactile elements.

While multiple embodiments are disclosed, still other embodiments of the present invention will become apparent to those skilled in the art from the following detailed description, which depicts and describes illustrative embodiments of the invention. As will be realized, the invention is capable of modifications in various aspects, all without departing from the scope of the present invention. Accordingly, the drawings and detailed description are to be regarded as illustrative in nature and not restrictive.

DETAILED DESCRIPTION

The following detailed description relates to stimulation of the human tongue for a variety of purposes. In one example, a tongue stimulation device may include a body to be placed entirely within a mouth of a user and atop the tongue of the user, an array of electrical (or electro-tactile) elements distributed on the body to stimulate corresponding areas of the tongue, a wireless receiver to receive stimulation information wirelessly from outside the mouth of the user, and at least one processing unit to transform the received stimulation information into a stimulation signal for each of the electro-tactile elements and to provide the stimulation signals to the electro-tactile elements. The use of wireless communication to receive the stimulation information at the at least one processing unit may allow more intensive processing of sensor information and other data to occur outside the environment of the mouth of the user, thus facilitating a small tongue stimulation device capable of residing entirely within the mouth without attaching the tongue stimulation device to components external to the mouth.

In other examples, the electrical elements may be supplemented or replaced by thermal elements that may heat or cool corresponding portions of tongue, and/or chemical elements that may provide one or more taste sensations to corresponding areas of the tongue. By combining two or more types of stimulation elements, the overall dynamic range of stimulation information that may be presented to the user via the tongue may be increased, thus allowing more varied types of information, such as, for example, audio information, to be presented via the tongue.

Other aspects and potential advantages of the embodiments disclosed herein are also presented below.

Figure 1:
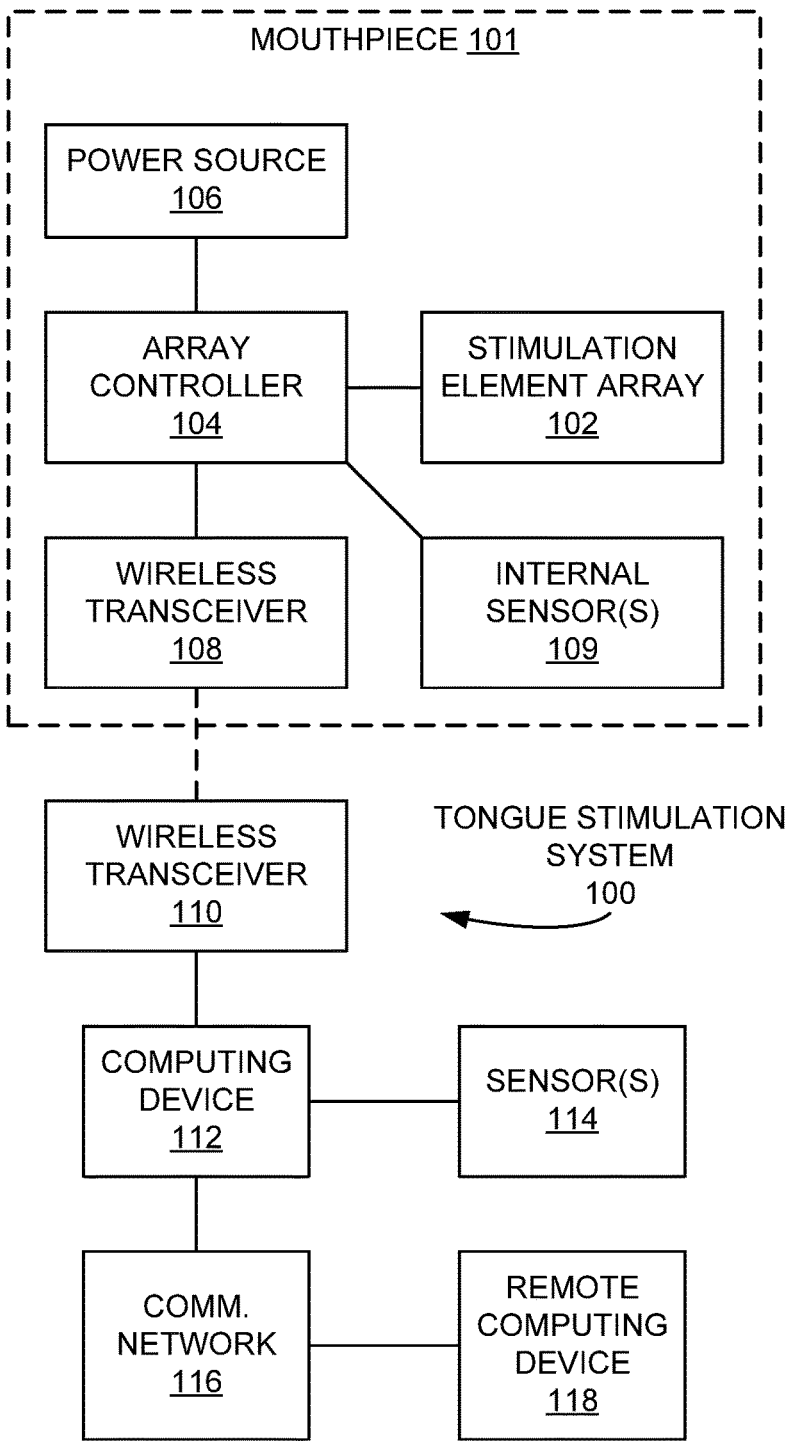
FIG. 1 is a block diagram of an example tongue stimulation system.

FIG. 1 is a block diagram of an example tongue stimulation system 100. The tongue stimulation system 100 may include a mouthpiece 101 or other body upon which a stimulation element array 102 is located such that each of the elements of the stimulation element array 102 is located adjacent to or proximate a corresponding area of the tongue of a user when the mouthpiece 101 is positioned upon an upper surface of the tongue. Also connected to, coupled with, or located on the mouthpiece 101 may be an array controller 104, a power source 106, and a wireless receiver or transceiver 108. As employed herein, a transceiver may operate as both a receiver and a transmitter. In addition, one or more internal sensors 109 also may be employed. Other components or devices, such as memory, discrete components (e.g., resistors, capacitors, etc.), and so on may also be included with the other components associated with the mouthpiece 101 in other examples.

In some examples, the tongue stimulation system 100 may also include components that are not mechanically attached or physically connected to the mouthpiece 101 or components located thereon, such as, for example, a second wireless transmitter or transceiver 110, one or more computing devices 112, one or more sensors 114, a communication network 116, and/or one or more remote computing devices 118. In some examples, each of the components 110-118 may be located external to the mouth of the user to minimize the amount of hardware attached or connected to the mouthpiece 101, thus potentially maximizing comfort of the user when wearing the mouthpiece 101.

Generally, the elements of the stimulation element array 102 may be positioned at distinct locations on the mouthpiece 101 so that each element may contact a corresponding area of the tongue when the user is wearing the mouthpiece 101. A graphical representation of an example stimulation element array 102 distributed about the mouthpiece 101 is provided in FIGS. 2A and 2B, described in greater detail below.

Each of the elements of the stimulation element array 102 may be, for example, an electrical (or electro-tactile) element, a thermal element, or a chemical element. As is discussed below, multiple types of elements (e.g., electrical, thermal, and chemical elements) may be employed to provide different types of tongue stimulation to distinct areas of the tongue simultaneously. Each of the different possible types of elements is discussed in greater detail below in conjunction with FIGS. 3-11.

The array controller 104 may be configured to control each of the elements of the stimulation element array 102 by providing at least one stimulation signal to each of the elements. Each of the stimulation signals may depend on the type of element (e.g., electrical, thermal, or chemical) being driven, the location of the element relative to the tongue of the user, the type of information to be relayed to the user via the tongue (e.g., visual information, audio information, and so on), stimulation information received via the receiver or transceiver 108, and other factors. In some embodiments, the array controller 104 may generate the stimulation information based on information stored internally with the array controller 104, on sensory information received from one or more internal sensors 109 located in the mouth of the user or other portion of the body of the user, and/or on other information. In one example, the array controller 104 may include a dedicated signal output for each stimulation signal to the generated. In another example, the array controller 104 may address some subset of the elements at any one time and provide the stimulation signals to the addressed elements during that time, followed by addressing and stimulating another subset of elements, possibly in a repeating fashion. In one example, the array controller 104 may be one or more microcontrollers or other algorithmic processors that execute a set of instructions to generate the stimulation signals. In another embodiment, the array controller 104 may be one or more hardware logic components, such as application-specific integrated circuits (ASICs) or other hardware logic devices. In yet other examples, the array controller 104 may include a combination of hardware, software, and/or firmware components or modules. The array controller 104 may also use various passive components (e.g., resistors, capacitors, electrodes, etc.) to provide the stimulation signals to the elements of the stimulation element array 102. In some examples, the array controller 104 may utilize one or more electronic components to control the voltage or current level of the stimulation signals, possibly including, but not limited to, one or more analog multiplexers.

The internal sensors 109 may be sensors located within the body of the user or, more specifically, within the mouth of the user. For example, the internal sensors 109 may detect salinity or other characteristics in the mouth of the user. In some embodiments, the internal sensors 109 may detect other chemicals, such as those associated with food being consumed by the user. In response to output from the internal sensors 109, the array controller 104 may generate, modulate, or alter the stimulation signals being provided to the stimulation element array 102, such as, for example, to enhance or reduce the ability of the user to taste a particular food or medication.

The power source 106 may be configured to deliver electrical power to the stimulation element array 102, the array controller 104, and/or receiver or transceiver 108 to facilitate the tongue stimulation described more fully below. In some examples, the power source 106 may be one or more batteries, capacitors, or other potential storage devices for electrical charge.

The receiver or transceiver 108 may be configured to receive stimulation information wirelessly from the transmitter or transceiver 110 located external to the mouth of the user, and to provide the received stimulation information to the array controller 104. The transceivers 108 and 110 may communicate over any wireless communication protocol, including, but not limited to, Wi-Fi® and Bluetooth®.

The transceiver 110 may be configured to receive the stimulation information from the computing device 112. Examples of the computing device 112 may include, but are not limited to, desktop computers, laptop computers, tablet computers, smartphones, gaming systems, and other processor-based systems. The computing device 112 may be configured to store previously generated stimulation information in memory and then provide the stimulation information via the transceiver 110 to the array controller 104, possibly in a repeating manner. In another example, the computing device 112 may generate the stimulation information on an ongoing basis, transmitting the stimulation information to the array controller 104 via the transceiver while generating new stimulation information, in a kind of pipelined manner. In some examples, the wireless transceiver 110 may be incorporated within the computing device 112. In other embodiments, the wireless transceiver 110 may be a Wi-Fi® router or wireless access point (WAP), or any other wireless transceiver or transmitter device.

Further, the generation of the stimulation information may be based on other information received by the computing device 112, such as, for example, sensor information received from one or more external sensors 114. Such sensors 114 may include, but are not limited to, audio or sound sensors, still image sensors, video or moving image sensors, touch or impact sensors, orientation sensors, inertial sensors, aroma sensors, chemical sensors, positioning systems (e.g., Global Positioning System (GPS)), and so on. In some embodiments, the computing device 112 may then generate stimulation information that represents the raw sensor data received from the one or more sensors 114. In other examples, the computing device 112 may process the received sensor data from the sensors 114 to generate stimulation information that represents some characteristic of the sensor data, or that represents other information contained within the sensor data. For example, the computing device 112 may generate data representative of a spoken language based on data from an audio sensor, such as a microphone, that captures audio or sound waves of human speech. In some embodiments, the computing device 112 may include one or more of the sensors 114, such as a smartphone that includes a microphone, camera, orientation sensors, GPS receiver, and the like.

In some examples, the computing device 112 may also receive the stimulation information, or information upon which the stimulation information is to be based, from a remote computing device 118 by way of a communication network 116, such as, for example, a local area network (LAN), a wide area network (WAN) (e.g., the Internet), a cellular network (e.g., a third generation (3G) or fourth generation (4G) network), or another communication network or connection. The remote computing device 118 may be, for example, a computer server or any other computing device, including those mentioned above in conjunction with the computing device 112. The data received from the remote computing device 118 may be the stimulation information to be provided to the array controller 104, or any data upon which the stimulation information is be based, possibly including stored information, sensor information, and so on.

In some examples, the transceiver 108 may also transmit information to the transceiver 110, which may receive and forward that information to the computing device 112 and/or the remote computing device 118. Such information may include, for example, output data from the internal sensors 109, diagnostic information generated by the array controller 104, and the like.

The electronic components employed in the mouthpiece 101, as described above, may be assembled using printed circuit boards, molded or printed plastics, and/or commercially available electronic components.

Figure 2A:
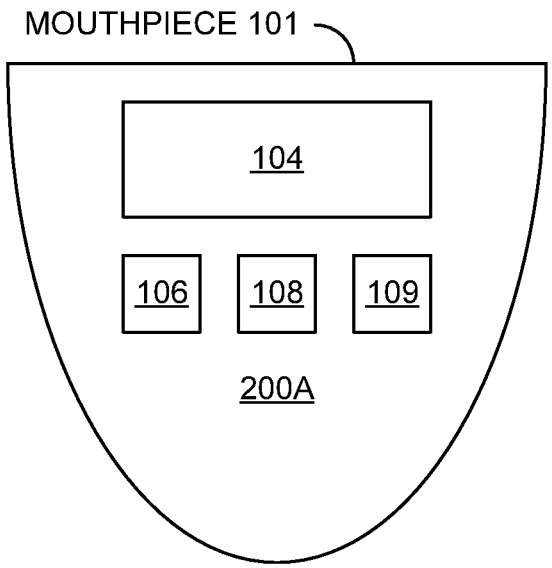
FIGS. 2A and 2B are graphical representations of an upper side and a lower side, respectively, of an example mouthpiece of the tongue stimulation system of FIG. 1.
Figure 2B:
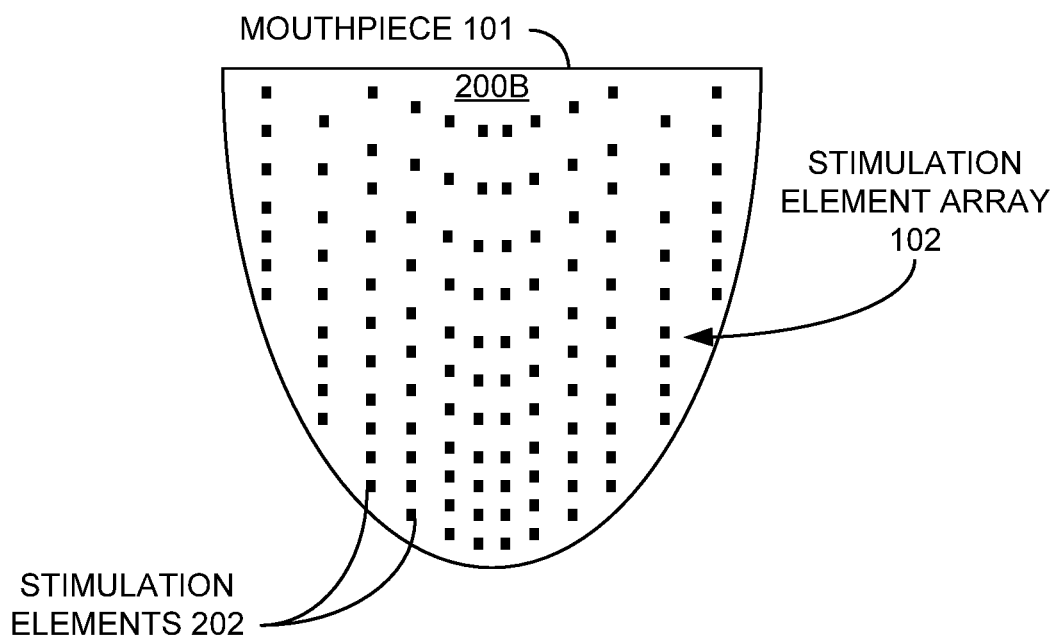

FIGS. 2A and 2B are graphical representations of an upper side 200A and a lower side 200B, respectively, of an example of the mouthpiece 101 of the tongue stimulation system 101 of FIG. 1. In this example, the mouthpiece 101 may be a polymer or composite material fashioned to be located atop the tongue of the user such that at least a majority of the top of the tongue contacts the mouthpiece 101. Other materials may be employed for the mouthpiece 101 in other embodiments. The mouthpiece 101 may also include one or more areas (not shown in FIGS. 2A and 2B) that may allow the user to clamp the mouthpiece 101 between upper and lower teeth to maintain the position of the mouthpiece 101 within the mouth. In some examples, the mouthpiece 101 may be heated or otherwise processed to allow the user to fashion the mouthpiece 101 to a shape that is comfortable for the user. In yet other examples, a scan or mold of the mouth and/or tongue of the user may be performed, with the resulting information from the scan or mold being used to manufacture a custom mouthpiece 101 for that particular user.

As shown in FIG. 2A, several of the components described earlier corresponding to the mouthpiece 101, such as, for example, the array controller 104, the power source 106, the transceiver 108, and/or the internal sensors 109, may reside on the upper side 200A. While FIG. 2A depicts a particular size and configuration for the components 104, 106, 108, and 109, other sizes and arrangements may be employed in other examples. Not shown, but possibly included in the components provided with the mouthpiece 101, are an on/off switch for the circuitry attached to the mouthpiece 101 that may be activated by a finger, teeth, lips, or tongue of the user. In other example, the power state of the mouthpiece 101 may be controlled externally and wirelessly, such as by way of a smartphone or other computing device 112. Further, the components associated with the mouthpiece 101 may be covered by a smooth layer of polymer or other material to render the mouthpiece 101 more comfortable to the user in some implementations. Further, the mouthpiece 101 could be molded from plastic, generated using a three-dimensional (3D) printer, or the like.

In FIG. 2B, individual stimulation elements 202 of the stimulation element array 102 are shown distributed on the lower side 200B of the mouthpiece 101 such that each stimulation element 202 corresponds to a particular area of the tongue of the user. In some examples, the stimulation elements 202 may be substantially arranged in rows, columns, or other arrangements in a regular manner. In other examples, such as that shown in FIG. 2B, the stimulation elements 202 may be arranged in higher densities, or may be of a smaller or larger area or size, in some areas of the tongue compared to other areas. For example, some areas of the tongue, such as the tip, may be more sensitive to electrical or thermal stimuli than others. Accordingly, more electrical and/or thermal stimulation elements may be grouped more densely near the tip of the tongue compared to other areas. In other embodiments, various areas of the tongue may be more sensitive to sour tastes, while other areas of the tongue may react more strongly to sweet tastes. As a result, in examples in which multiple types of stimulation elements are employed, each type of element may or may not be grouped differently over the surface of the tongue to be stimulated. Electrodes for electrical stimulation elements could be manufactured as part of a printed circuit board (e.g., a flexible printed circuit board that may conform to the shape of the tongue), by sputter-coating materials onto the mouthpiece 101, by electroplating the electrodes onto the mouthpiece 101, by 3D-printing the electrodes, or the like. Chemical stimulation elements may be fabricated using 3D-printing, sputter-coating, electrochemical plating, injection molding, or other techniques. Thermal stimulation elements may be fabricated using many of these same manufacturing processes.

Figure 3:
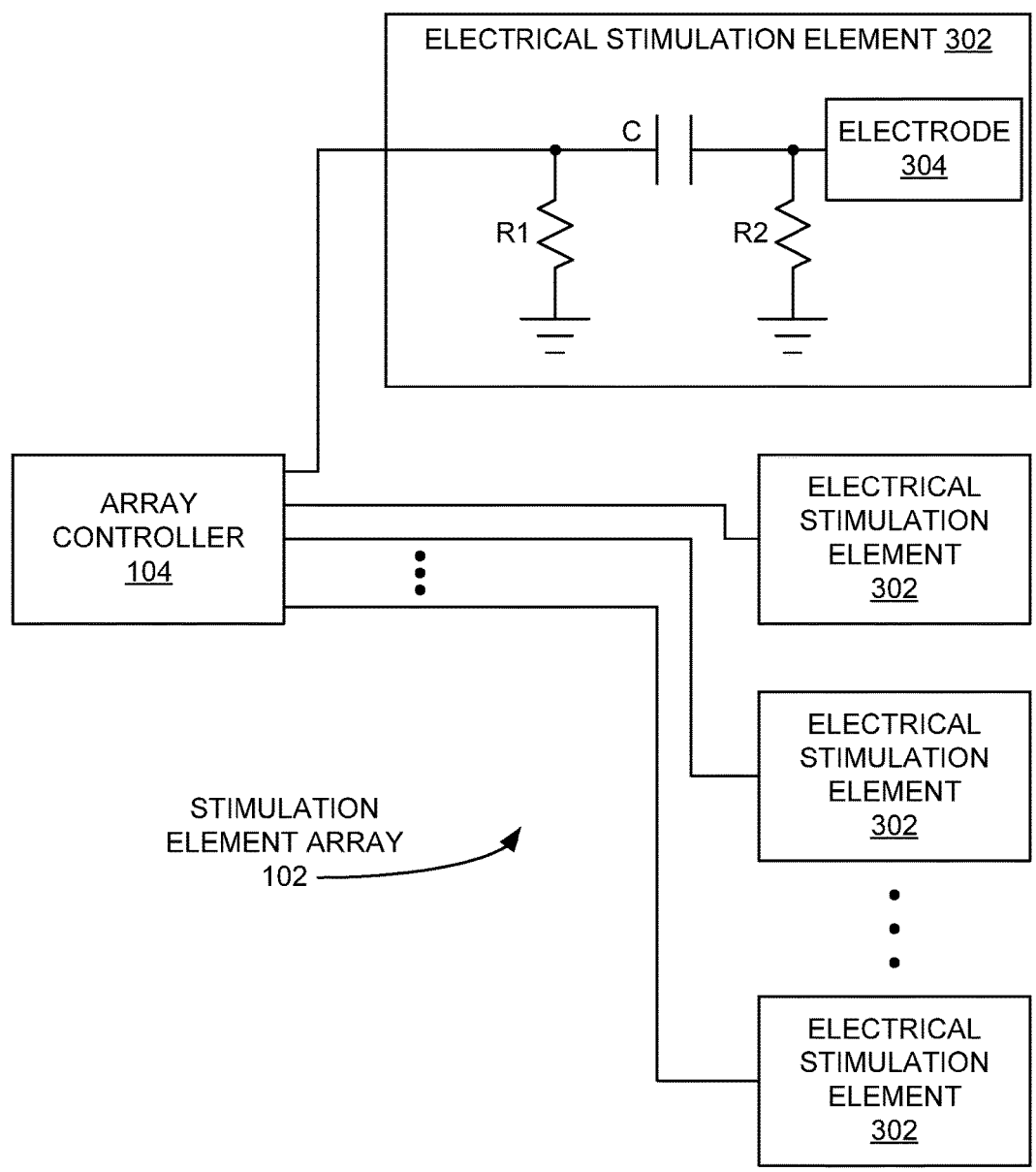
FIG. 3 is a block diagram of an example stimulation element array of the tongue stimulation system of FIG. 1 in which the stimulation elements are electrical or electro-tactile stimulation elements.

FIG. 3 is a block diagram of an example stimulation element array 104 of the tongue stimulation system 100 of FIG. 1 in which the stimulation elements are electrical or electro-tactile stimulation elements 302. In one example, the electrical stimulation elements 302 are configured to apply a voltage across, or supply an electrical current through, a corresponding area of the tongue to elicit a tactile response at that area. More specifically, FIG. 3 illustrates a particular electrical stimulation element 302 in which a capacitor C couples an output of the array controller 104 to an electrode 304 configured to contact an area of the tongue. Also in this example, each of two resistors R1 and R2 couple opposing ends of the capacitor to ground. However, in other embodiments, the electrical stimulation element 302 may incorporate circuits other than that shown in FIG. 3.

In an example, an output of the array controller 104 may provide stimulation signals that include multiple bursts of voltage pulses to the electrode 304 to elicit the intended magnitude and duration of tactile sensation desired at the affected area of the tongue. Further, the array controller 104 may be employ different lengths of bursts and/or pulses for different stimulation elements 302, and vary the stimulation signal for each element over time to relay stimulation information to the various areas of the tongue.

In other examples, the electrical or electro-tactile stimulation element 302 may be a MEMS (microelectromechanical system) device that provides some stimulation, such as a vibration of a particular frequency and/or magnitude, in response to an electrical stimulation signal provided to the element 302. In some examples, the frequency and/or magnitude of the vibration may be varied in response to particular changes in the stimulation signal.

Figure 4:
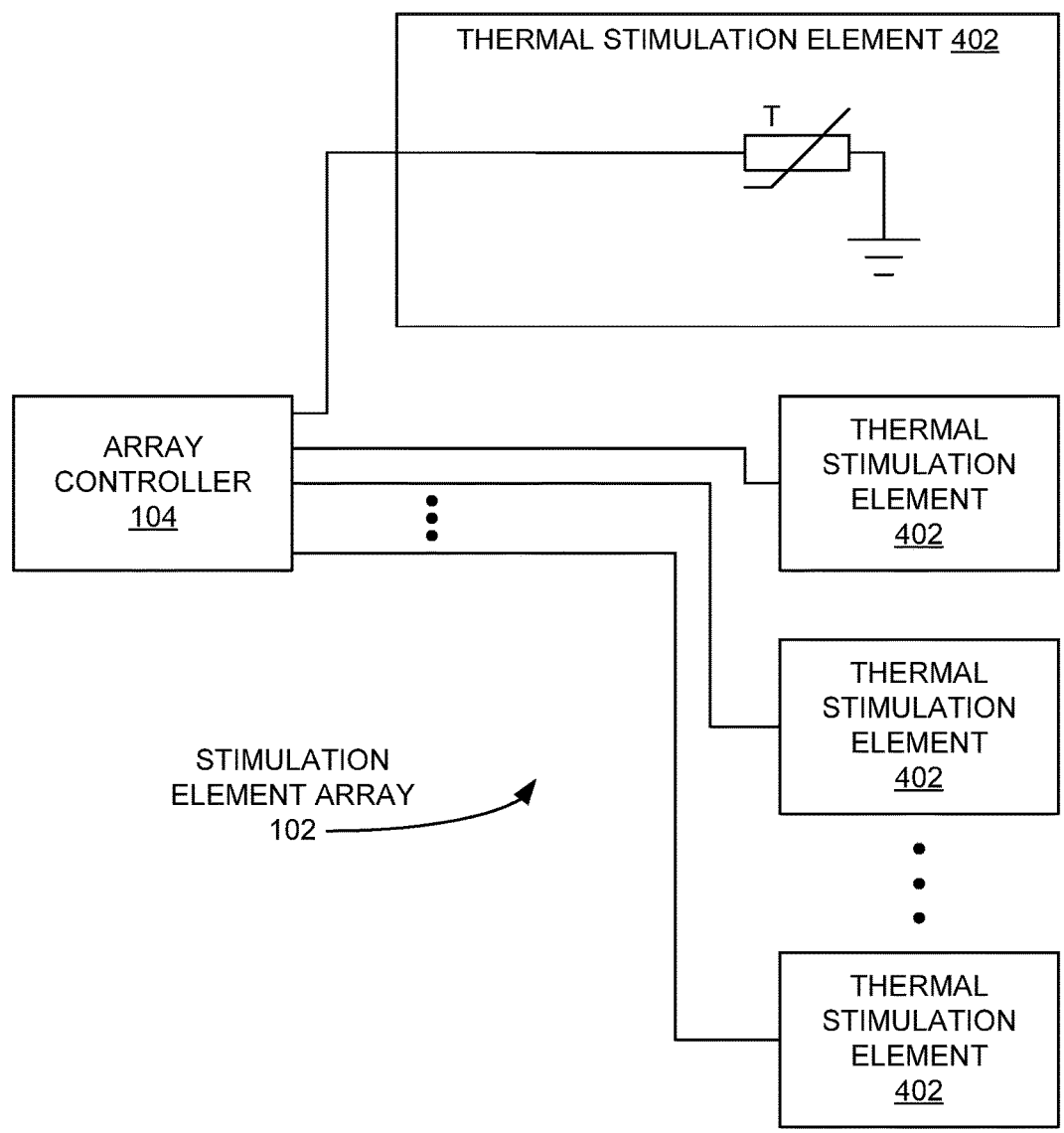
FIG. 4 is a block diagram of an example stimulation element array of the tongue stimulation system of FIG. 1 in which the stimulation elements are thermal stimulation elements.

FIG. 4 is a block diagram of an example stimulation element array 104 of the tongue stimulation system 101 of FIG. 1 in which the stimulation elements are thermal stimulation elements 402. In this example, one or more of the thermal stimulation elements 402 may include a thermistor T being operated as a heating element. In some embodiments, the thermistor T is a positive temperature coefficient (PTC) thermistor. However, other types of heating elements that may be employed in the stimulation element array 102 to heat a corresponding area of the tongue for a controllable period of time may be used in other embodiments. In some embodiments, the thermal stimulation elements 402 may be cooling elements that cool a corresponding area of the tongue for some time period. Moreover, the thermal stimulation elements 402, such as, for example, Peltier elements or other thermoelectric heat pump devices may be configured to heat or cool an adjacent area of the tongue at varying times. In some examples, such heating/cooling elements may be driven by a corresponding stimulation signal such that periods of heating or cooling may be followed by a counteracting process to return that area of the tongue to a more normal or average temperature, thus possibly increasing the frequency at which the thermal stimulation element 402 may be operated.

Figure 5:
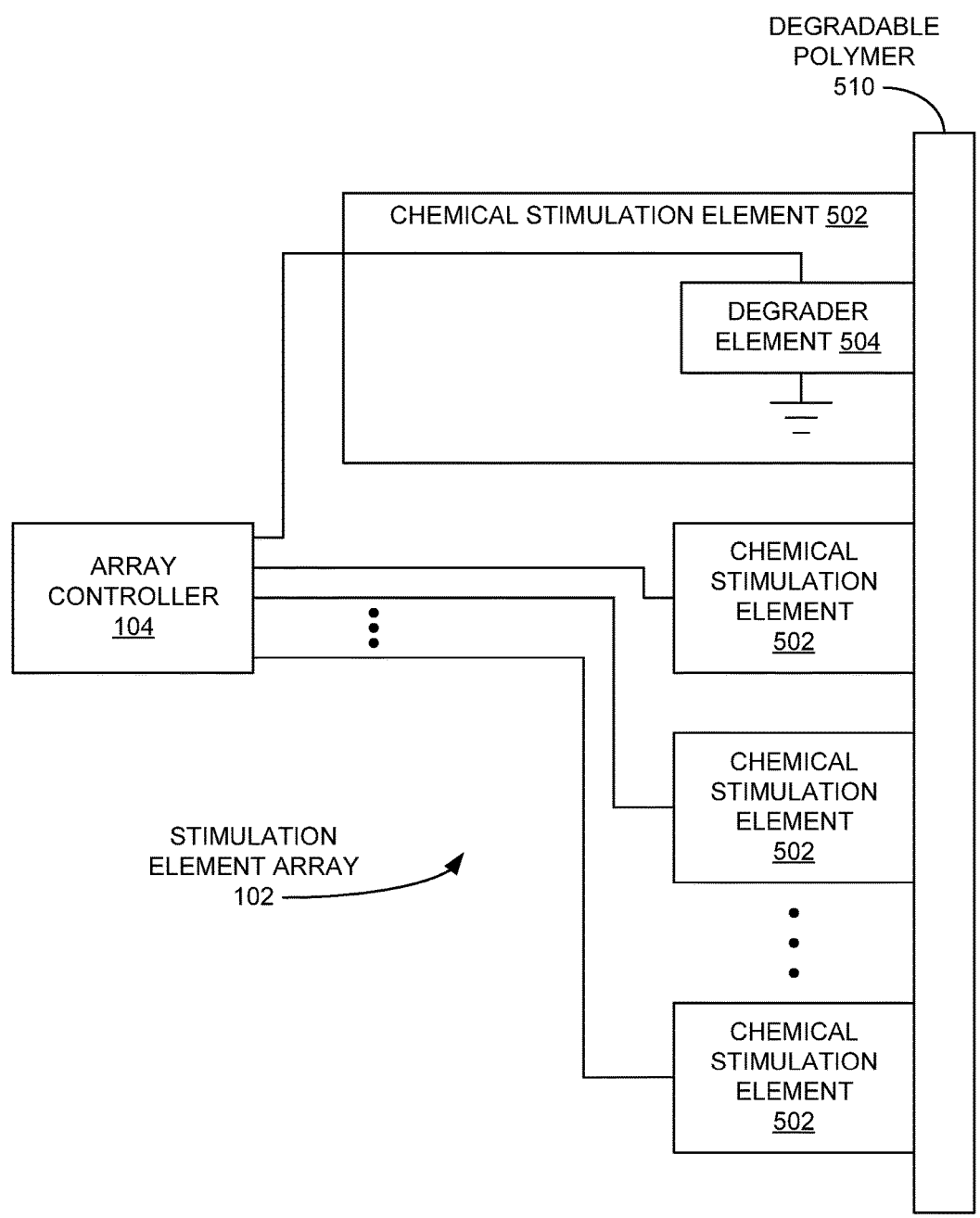
FIG. 5 is a block diagram of an example stimulation element array of the tongue stimulation system of FIG. 1 in which the stimulation elements are chemical stimulation elements that employ a degradable polymer.
Figure 6:
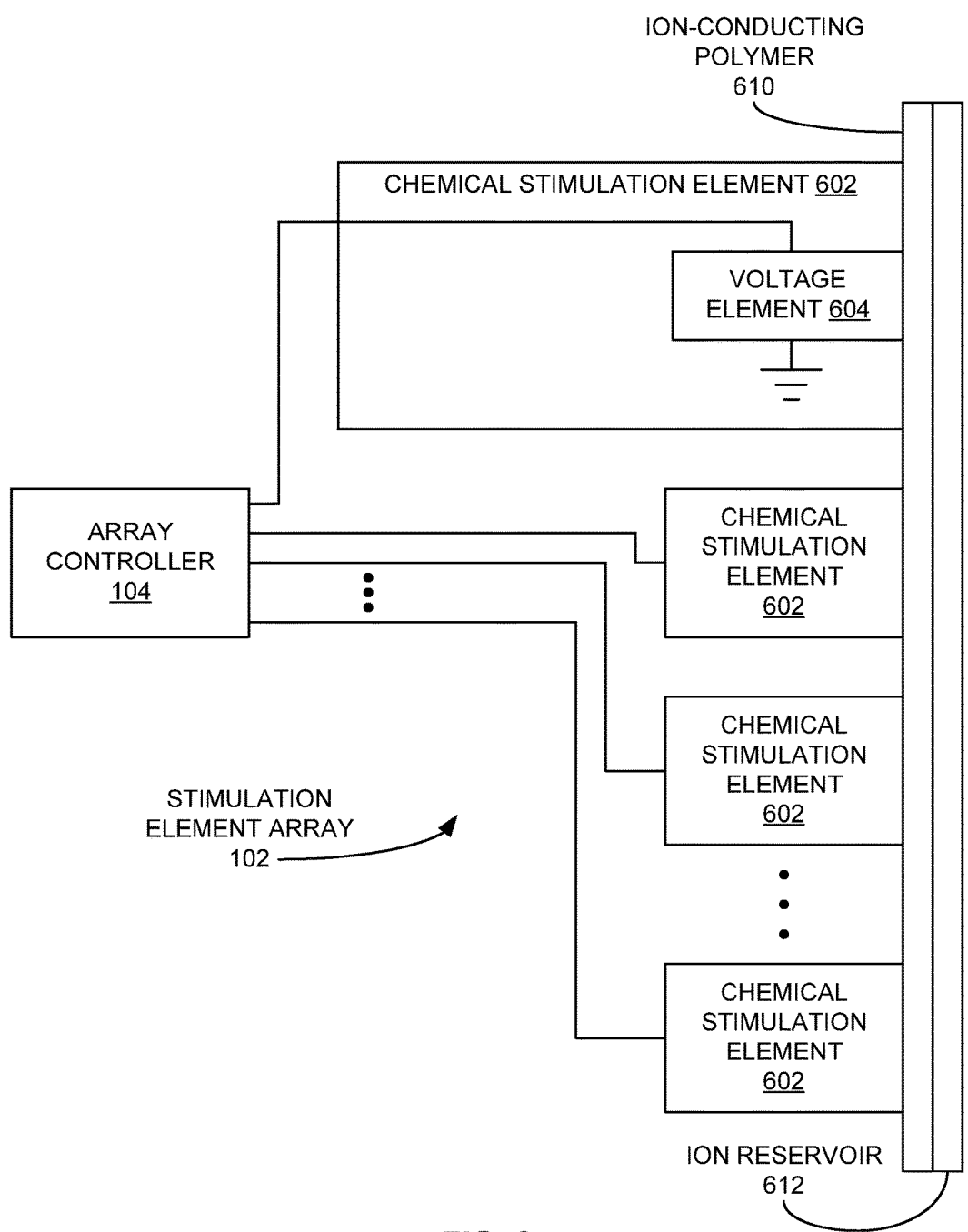
FIG. 6 is a block diagram of an example stimulation element array of the tongue stimulation system of FIG. 1 in which the stimulation elements are chemical stimulation elements that employ an ion-conducting polymer.
Figure 7:
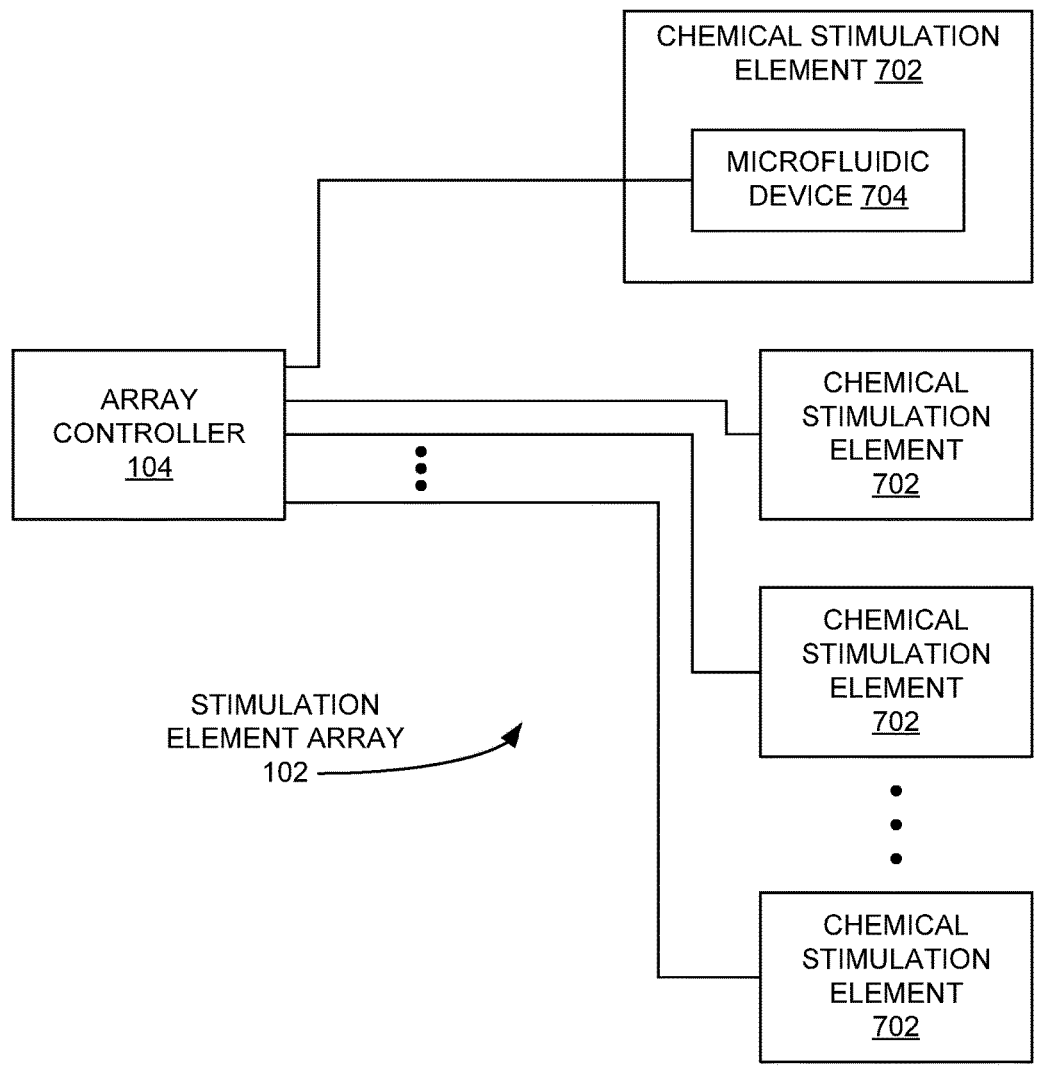
FIG. 7 is a block diagram of an example stimulation element array of the tongue stimulation system of FIG. 1 in which the stimulation elements are chemical stimulation elements that employ microfluidic devices.

FIGS. 5, 6, and 7 are block diagrams of example types of stimulation element arrays 102 of the tongue stimulation system of FIG. 1 in which the stimulation elements are chemical stimulation elements. Such elements may cause one or more types of tastes to be experienced by a corresponding area of the tongue by application of a particular chemical. Moreover, in some examples, the amount or concentration of the chemical being applied may result in a stronger taste, thus providing a means of imparting magnitude information to the user. In some examples, the chemical stimulation elements may enhance or inhibit the operation of areas of taste buds, such as by stimulating, enhancing, diminishing, or paralyzing the operation of the particular taste buds. Further, in some embodiments, the effects of the imposed taste, enhancement, or inhibition may be actively reversed using the chemical stimulation element, such as by way of flushing the imposed chemical or changing the composition of the chemical.

For example, FIG. 5 is a block diagram of an example stimulation element array 102 in which the stimulation elements are chemical stimulation elements 502 that employ a degradable polymer 510. In one example, the degradable polymer 510 includes a material that does not possess a particularly strong or recognizable taste. In this embodiment, each of the chemical stimulation elements 502 may include one or more degrader elements 504, which may include a heating element that applies heat to the degradable polymer 510, an electrode that applies a voltage or current to the degradable polymer 510, or another type of element that, when activated, causes degradation or fragmentation of the degradable polymer 510 into at least one chemical functional group that may be detected as a taste (e.g., sour, sweet, salty, etc.) by an area of the tongue corresponding to the portion of the degradable polymer 510 being degraded. In the particular example of FIG. 5, the degradable polymer 510 is depicted as a layer of material located between the tongue and the stimulation element array 102, such that activation of a particular chemical stimulation element 502 causes the portion of the degradable polymer 510 adjacent thereto to degrade, thus providing an intended taste to the portion of the tongue opposite the activated chemical stimulation element 502 from the degradable polymer 510. In other embodiments, each of a plurality of portions of the degradable polymer 510 may be located adjacent to a corresponding chemical stimulation element 502. Other configurations of the chemical stimulation elements 502 and the degradable polymer 510 relative to the user tongue may be utilized in other implementations.

FIG. 6 is a block diagram of another example stimulation element array 102 of the tongue stimulation system 100 of FIG. 1 in which the stimulation elements are chemical stimulation elements 602 that employ an ion-conducting polymer 610 and an ion reservoir 612. In this particular example, each chemical stimulation element 602 may include a voltage element 604, such as a pair of electrodes that may apply a voltage differential across an area of the ion-conducting polymer 610 in response to a stimulation signal from the array controller 104. The voltage differential allows ions from the ion reservoir 612 to pass from the reservoir 612, through the ion-conducting polymer 610, to a specific area of the tongue. The application of the ion to an area of the tongue may cause that area to be exposed to a particular taste, or for the tasting capability of that area to be enhanced or reduced, depending on the nature of the ion. As shown in FIG. 6, a single ion reservoir 612 and a single layer of ion-conducting polymer 610 may be laid atop the stimulation element array 102 so that activation of a chemical stimulation element 602 causes ions from the reservoir 612 to pass downward through the ion-conducting polymer 610 onto the corresponding area of the tongue. In other examples, an individual ion reservoir 612 and associated ion-conducting polymer 610 may be employed for each chemical stimulation element 602, such that each chemical stimulation element 602 may include a voltage element 604, an ion-conducting polymer 610, and an ion reservoir 612.

FIG. 7 is a block diagram of another example stimulation element array 102 of the tongue stimulation system 100 of FIG. 1 in which the stimulation elements are chemical stimulation elements 702 that employ microfluidic devices 704, such as, for example, paper-based microfluidic devices, polymer-based microfluidic devices (e.g. poly(methyl methacrylate), or PMMA), or some hybrid thereof. In some examples described in greater detail below, the microfluidic device 704 may be employed to electrolyze water. However, instead of electrolyzing water to generate hydrogen ($H_2$) and oxygen ($O_2$), as is a typical use of the electrolysis of water, the microfluidic device 704 may be employed to create a point or area of low pH, which may be detected by taste buds in the area as a sour taste.

Figure 8:
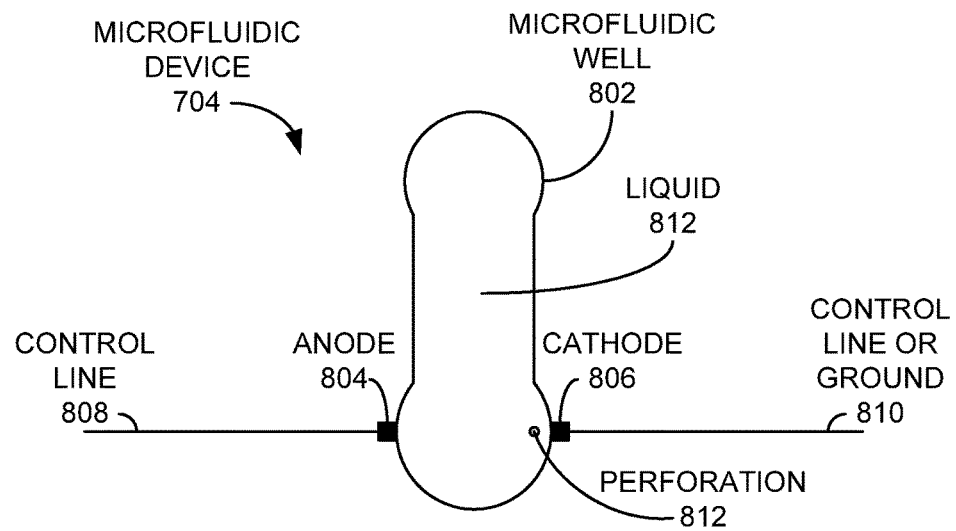
FIG. 8 is a graphical representation of an example microfluidic device that may be employed in the example stimulation array of FIG. 7.

FIG. 8 is a graphical representation of an example microfluidic device 704 that may be employed in the example stimulation array 102 of FIG. 7 to generate areas of sour taste. The microfluidic device 704 may include a microfluidic well 802 coupled to a first control line 808 by way of an anode 804 and coupled a second control line (or ground) 810 via a cathode 806. The microfluidic well 802 may be filled with a liquid 812, such as water, although other aqueous conductive solutions, such as a solution at least similar to human saliva, may be employed in other examples. Using the control lines 808 and 810 driven by the array controller 104, a direct-current (DC) voltage potential may be applied across the microfluidic well 802 via the anode 804 and cathode 806. More specifically, the anode 804 may have a higher voltage than the cathode 806 to create an electric field within the well 802. In response to the applied voltage, protons (or $H^+$ ions) may collect at the cathode 806 and hydroxide (or $OH^-$ ions) may collect at the anode 804, instead of hydrogen and oxygen gas. The presence of the protons may be sensed as a sour taste at the location of the tongue at which the microfluidic well 802 is located. In one example, the microfluidic well 802 may include a perforation 812 near the cathode 806 to allow some of the protons to pass outside the microfluidic well 802 to contact the tongue.

In some examples, the polarity of the voltage applied at the anode 804 and the cathode 806 via the control lines 808 and 810 may be swapped to reverse the electrolysis reaction, thus reducing the number or concentration of protons present. As a result, the resulting sour taste may be removed quickly from the affected area of the tongue.

Figure 8A:
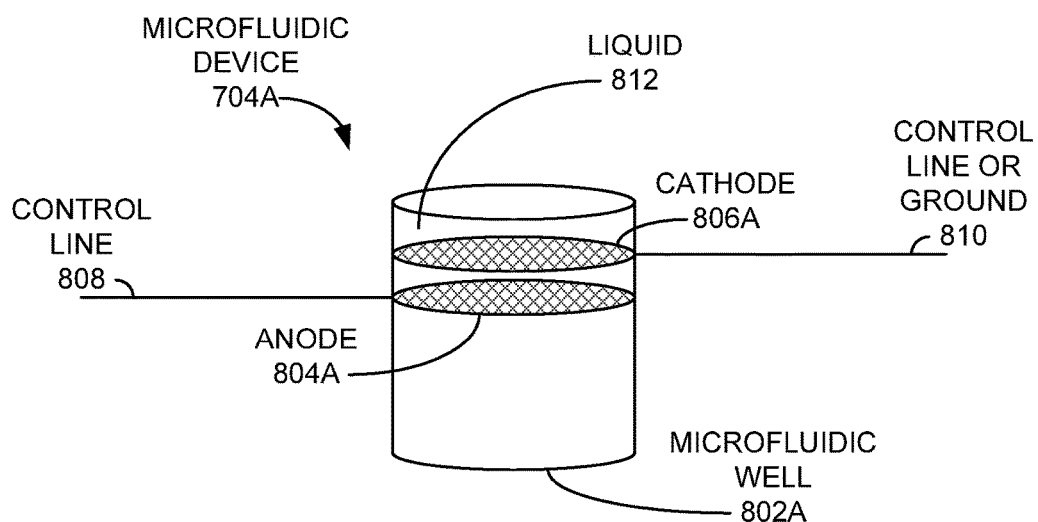
FIG. 8A is a graphical representation of another example microfluidic device that may be employed in the example stimulation array of FIG. 7.

FIG. 8A is a graphical representation of another example microfluidic device 704A that may be employed in the example stimulation array of FIG. 7. In this particular example, the microfluidic device 704A includes a small microfluidic well 802A, which may be cylindrical in some examples, but may take on other three-dimensional shapes in other embodiments. Moreover, the microfluidic well 802A may be open at a top end. Located within the microfluidic well 802A may be a liquid, such as water, saliva, or another aqueous conductive solution, as indicated above. In addition, located within the well 802A may be an anode 804A and a cathode 806A near the top end of the well 802A. In the particular example of FIG. 8A, each of the anode 804A and the cathode 806A are electrically conductive screens driven by the first control line 808 and the second control line or ground 810, respectively. In response to the anode 804A being driven to a higher voltage than the cathode 806A, an electric field may be created therebetween, causing protons to collect at or near the cathode 806A and hydroxide to collect at or near the anode 804A. The increased concentration of protons near the open top of the microfluidic well 802A may then be detected by an adjacent area of the tongue, possibly as a sour taste.

While the microfluidic well 802A is described above as being open near the top end, with the anode 804A and the cathode 806A located within the well 802A near the top end, other configurations for the well 802A, the anode 804A, and the cathode 806A are also possible. In one embodiment, the microfluidic well 802A may be open near a bottom thereof, with the anode 804A and the cathode 806A located within the well 802A near that bottom end, and with the cathode 806A positioned below the anode 804A. In yet other examples, the microfluidic well 802A may be configured as a pore with both bottom and top open ends, and with the well 802A being filled with the saliva of the user.

Figure 9:
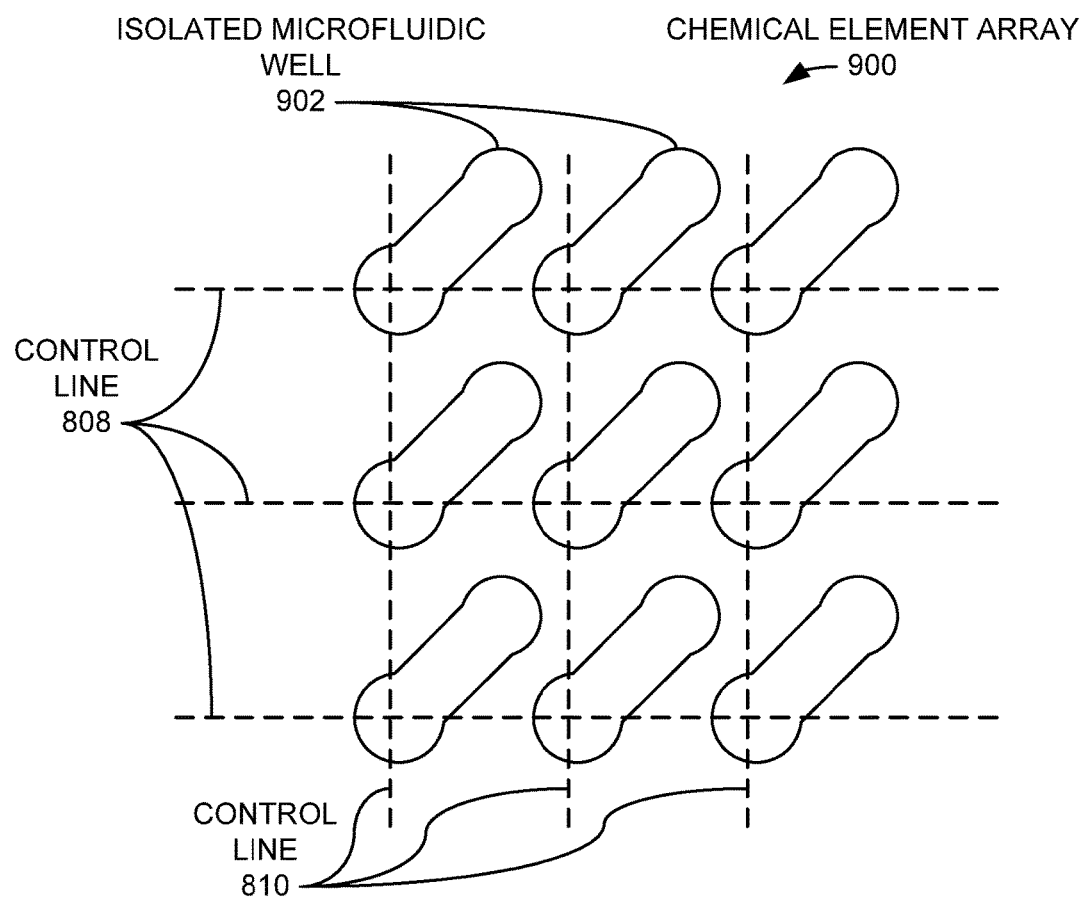
FIG. 9 is a graphical representation of an example chemical element array employing isolated microfluidic wells.

FIG. 9 is a graphical representation of an example chemical element array 900 employing a plurality of isolated microfluidic wells 902. As opposed to providing each microfluidic well 902 with a separate pair of control lines 808 and 810, a plurality of first control lines 808 and a plurality of second control lines 810 may be employed such that a selection of a single first control line 808 and a single second control line 810 causes the application of the DC activating voltage across a single isolated microfluidic well 902. In one example, the plurality of first control lines 808 may lie along a first side of the array of isolated microfluidic wells 902, while the plurality of second control lines 810 may line along a second side of the array of isolated microfluidic wells 902 to apply the voltage across the wells 902, as depicted in FIG. 9. As a result of such an embodiment, an array of 100 isolated microfluidic wells 902 arranged in a ten-by-ten array may require only ten first control lines 808 and ten second control lines 810, or twenty control lines total, as opposed to a dedicated first control line 808 and second control line 810 for each well 902, or 200 control lines 808 and 810 total.

Figure 10:
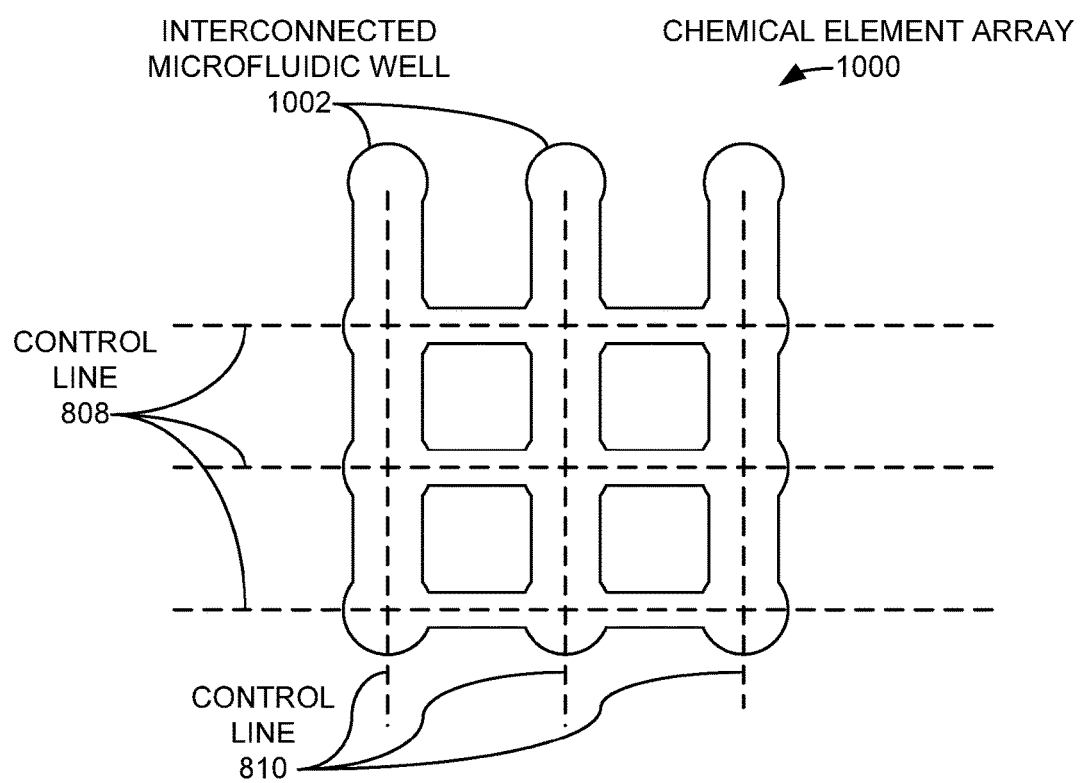
FIG. 10 is a graphical representation of an example chemical element array employing interconnected microfluidic wells.

FIG. 10 is a graphical representation of an example chemical element array 1000 employing a plurality of interconnected microfluidic wells 1002. An array of this type may be easier to manufacture due to the interconnected microfluidic wells 1002 essentially forming a single fillable well. As illustrated, this chemical element array 1000 may be driven using a similar structure of the first control lines 808 and the second control lines 810 as depicted in FIG. 9. If the outputs of a microcontroller or similar device are employed to drive the first control lines 808 and the second control lines 810, each of the control lines 808 and 810 that are not being selected at a particular point in time may be in a high impedance state, as opposed to a low or high voltage level, as described above. Consequently, diodes or resistors may be employed to couple the control lines 808 and 810 to a known reference voltage, or to ensure that a voltage differential is not being applied across an unselected microfluidic well 902 and 1002. For example, at each well 902 and 1002, a diode may couple the first control line 808 and the second control line 810 to ensure the voltage across the well 902 and 1002 is biased properly when the control lines 808 and 810 are not being driven to prevent undesirable activation of the well 902 and 1002.

In some embodiments of the chemical stimulation elements 502, 602, and 702 of FIGS. 5-7, including the microfluidic wells 802, 902, and 1002 of FIGS. 8-10, a microfluidic pump may be employed in conjunction with each chemical stimulation element 502, 602, and 702 to remove or reverse the effect of the chemical stimulation being used. For example, the microfluidic pump, driven by an output of the array controller 104, may be employed to flush water or another chemical onto the affected area of the tongue to remove the protons or chemicals applied to the tongue by the corresponding chemical stimulation element 502, 602, and 702.

Figure 11:
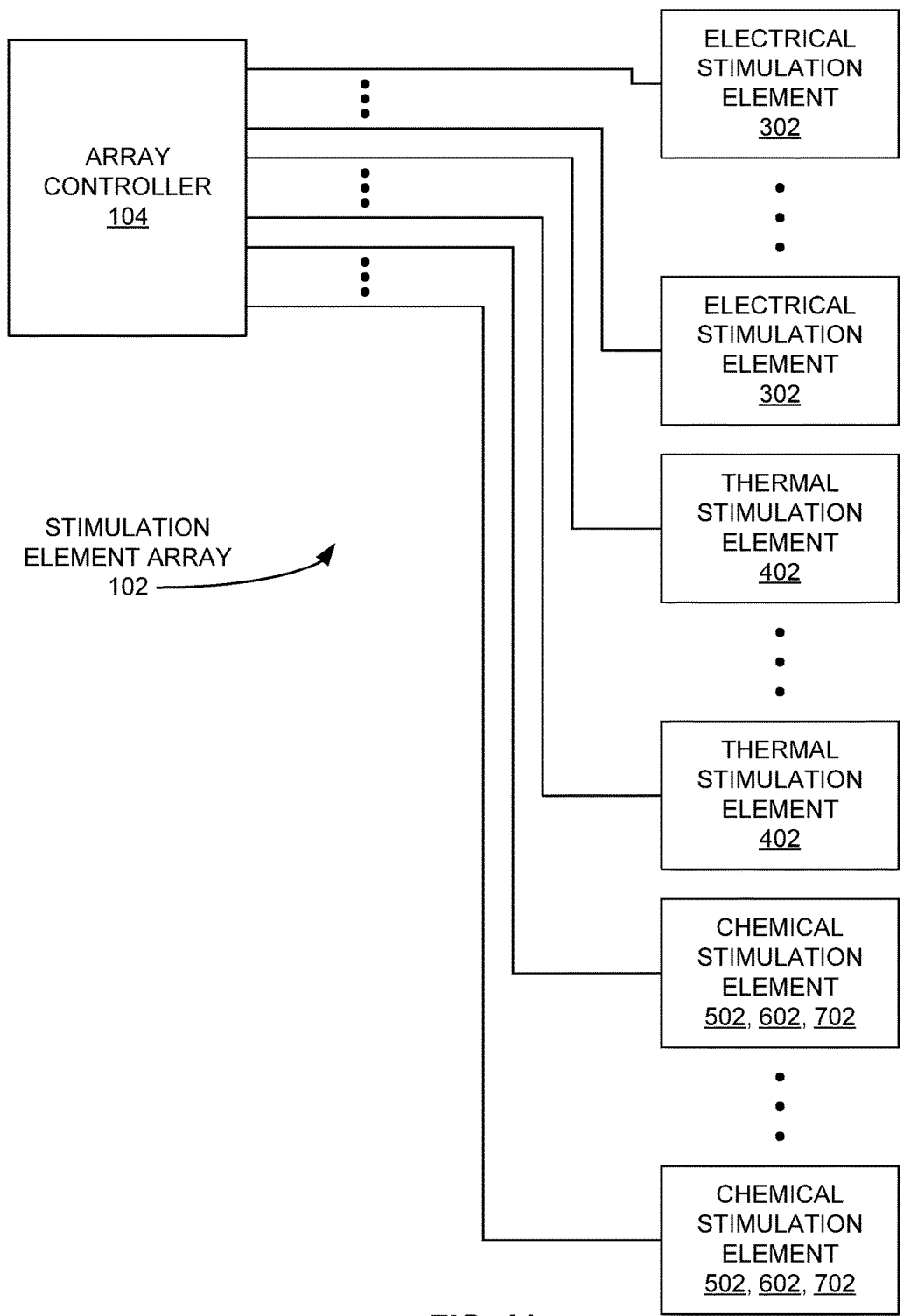
FIG. 11 is a block diagram of an example stimulation element array of the tongue stimulation system of FIG. 1 in which the stimulation elements include electrical, thermal, and chemical stimulation elements.

FIG. 11 is a block diagram of an example stimulation element array 102 of the tongue stimulation system 100 of FIG. 1 in which the stimulation elements include a combination of two or more of the electrical stimulation elements 302, thermal stimulation elements 402, and the chemical stimulation elements 502, 602, and 702. Additionally, the use of multiple types of the chemical stimulation elements 502, 602, and 702 described earlier may result in the ability to apply a variety of tastes to each particular area of the tongue associated with those elements 502, 602, and 702. Overall, the use of multiple types of the stimulation elements 302, 402, 502, 602, and 702 may result in the ability to provide a greater dynamic range of information to the user via the tongue over a particular period of time.

In some embodiments, the array controller 104 may employ multiple processors to facilitate parallel generation of the various stimulation signals being provided to the stimulation elements 302, 402, 502, 602, and 702. For example, the stimulation signals for the electrical stimulation elements 302 may be generated by one or more different processors than those used to generate the stimulation signals for the thermal stimulation elements 402 and/or the chemical stimulation elements 502, 602, and 702. Moreover, multiple processors may be employed for a single type of stimulation element 302, 402, 502, 602, and 702. For example, each of a number of processors may be employed to generate the stimulation signals for a distinct subset of the electrical stimulation elements 302, the thermal stimulation elements 402, and/or the chemical stimulation elements 502, 602, and 702.

To optimize the effectiveness of the stimulation element array 102 in delivering information to the user via the tongue, an example of the stimulation element array 102 may be configured to perform lingual nerve mapping or perception mapping experiments on a user or multiple users to determine some optimum location for the electrical, thermal, and/or chemical stimulation elements to be used, as well as other characteristics of the stimulation element array 102 and the array controller 104. In some examples, the array controller 104 or the computing device 112 may be configured to generate series or sets of predetermined stimulation signals or stimulation information, respectively, to determine sensitivity with respect to electrical, thermal, and/or chemical stimuli at various areas of the tongue. More specifically, the stimulation information used to generate the stimulation signals to the elements of the stimulation element array 102 may be configured to determine a relative sensitivity of each area of the tongue associated with a corresponding stimulation element. In one example, the elements may be spaced relatively closely so that a detailed nerve map or perception map of the tongue of one or more users may be made. The sensitivity may be determined by sensors located close or adjacent to the stimulation elements that may measure or detect the effect of the stimulation by the corresponding element. In other examples, the sensitivity may be determined by way of feedback (verbal, for instance) provided by the user in response to stimulation by each element of the stimulation element array 102.

In testing various areas of the tongue, the computing device 112 or the array controller 104 may be configured to vary the magnitude and/or frequency of the stimulation signals applied to each of the elements of the stimulation element array 102 to determine the sensitivity of each area of the tongue to such factors or characteristics of the stimulation signals. In addition, series of stimulation signals applied to each area may be generated to determine a recovery time during which an additional stimulation of a particular stimulation element after a previous stimulation is not likely to be perceived fully by the corresponding area of the tongue.

In some embodiments, the computing device 112 or the array controller 104 may be configured to conduct nerve density tests that determine a minimum discrimination distance of various areas of the tongue of a user. To determine such a distance, the computing device 112 or the array controller 104 may be configured to activate sets of differently spaced pairs of elements of the stimulation element array 102 at different times. In response to the activation of each pair, the user may be asked to identify whether the activation is sensed as two closely spaced, but separate, activations, or as just a single activation. The closest distance between an activated pair sensed by the user at a particular area of the tongue may then be determined to be the minimum discrimination distance for that area. Such tests may also be performed at various frequencies and/or intensities to determine if the minimum discrimination distance for various areas of the tongue is based on such factors. Based on such tests, a stimulation element array 102 may be designed such that elements are more closely distributed in areas of shorter minimum discrimination distances.

In other examples, the computing device 112 or the array controller 104 may be configured to perform frequency bin experiments, during which the stimulation signals for each element of the stimulation element array 102 may exhibit various frequencies. Based on these experiments, each area of the tongue may be associated with one or more different bands of frequencies based on how easily those frequencies are perceived by the user at that area. Based on that information, different frequency bins or bands may be associated with one or more specific areas of the tongue. Accordingly, each such area may be stimulated using one or more frequencies of its associated frequency bin, thus maximizing the perception of the user to stimuli at each of those areas. In some examples, the bins may be defined according to a logarithmic scale, a linear scale, or a binary or octave scale. In other examples, the frequency bins may be defined according to the Greenwood function, which correlates hair cell locations within the inner ear to frequencies that correspond with their associated auditory neurons, as such a relationship may be particularly effective in associating particular audio frequencies to certain areas of the tongue.

Based on the determined sensitivities of each area of the tongue to the stimulation, a lingual nerve or perception map may be generated from which an optimal physical pattern for the stimulation element array 102 and associated stimulation signals for the particular user may be determined. In some examples, the lingual nerve or perception map may also be used to determine a particular physical size or area for each of the elements of the stimulation element array 102, as the size of a particular stimulation element (e.g., an electrode for an electrical stimulation element 302) may correspond to the perceived intensity of the stimulus for that element. For example, areas of the tongue that are less sensitive to particular types of stimulus may be associated with larger elements, and vice versa. Potential aspects of such a map may include associating various minimum and/or maximum detectable signal magnitudes, minimum and/or maximum detectable signal frequencies, minimum discrimination distances, minimum and/or maximum recovery times, and other aspects to each area of the tongue. In some examples, this mapping information may be combined with mapping information corresponding to other users to generate an average lingual nerve or perception map. That map may then be employed to provide an optimal stimulation element array 102 pattern, element size, and/or associated stimulation signals for a plurality of users. In either case, such mapping may render presentation of information via the tongue more efficient, thus potentially providing a greater dynamic range of information capable of being presented to the user via the tongue.

For a stimulation element array 102 having more than one type of stimulation element (e.g., two or more of electrical, thermal, and chemical stimulation elements), at least some elements of one type may be located at different areas of the mouthpiece 101 than some elements of a different type and may be stimulated using different frequencies, magnitudes, and so on. For example, some areas of the tongue may be more sensitive to electro-tactile stimulus than thermal stimulus. Further, if differing types of chemical stimulation elements (e.g., chemical stimulation elements 502, 602, and 702) are employed in the stimulation element array 102, the chemical stimulation elements of different types may be optimally placed in different locations about the tongue of the user.

Figure 12:
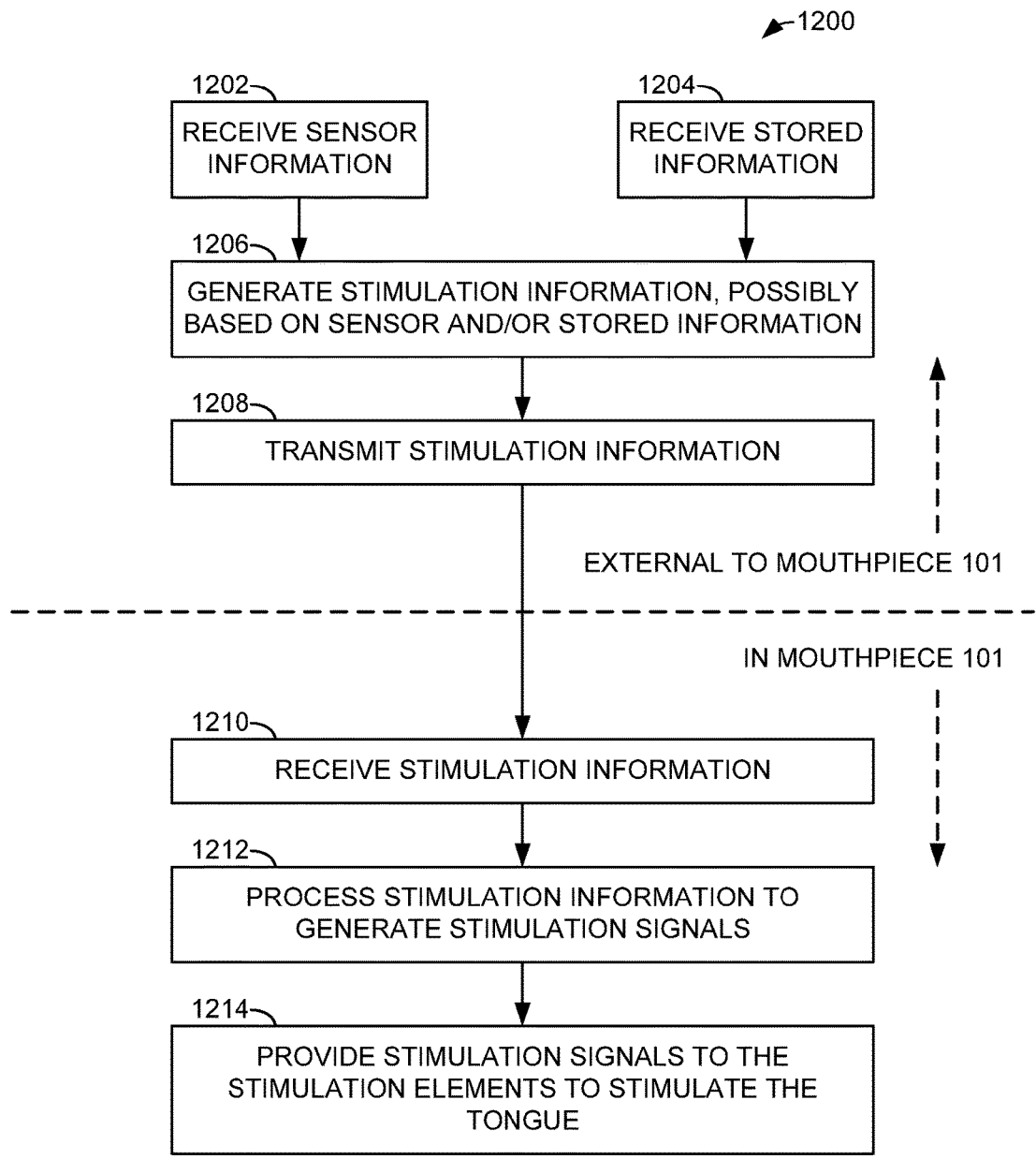
FIG. 12 is a flow diagram of an example method of stimulating the tongue of a user.

FIG. 12 is a flow diagram of an example method 1200 of stimulating the tongue of a user. While the method 1200, as well as other methods presented below, is described herein as being performed using the tongue stimulation system 100 of FIG. 1, other systems or devices not specifically discussed herein may also be employed to perform the method 1200 in other embodiments.

In the method 1200, the computing device 112 may receive sensor information from the one or more sensors 114 (operation 1202). Such information may include, but is not limited to, audio information, light or image information, touch or pressure information, thermal or temperature information, inertial information, aroma information, chemical information, and so on. The computing device 112 may also receive, access, or retrieve previously stored information, such as from a local data storage device or system, or from the remote computing device 118 or associated data storage device or system via the communication network 116. Such information may include, for example, translations from one spoken language to another, information regarding known therapeutic audio patterns, and any other database of information. In some embodiments, multiple sensors of a single type of sensor, such as multiple microphones, may be employed to provide multiple source information, such as stereo sound.

The computing device 112 may generate stimulation information (operation 1206). In some examples, the computing device 112 may process one or both of sensor information (from operation 1202) and received information (from operation 1204) to generate the stimulation information. In some embodiments, the generated stimulation information may include a direct representation of the sensor information or stored information. In other examples, the generated stimulation information may represent some transformed version of the received sensor information based on stored information. The computing device 112, in yet other examples, may generate other types of stimulation information based on one or both of the sensor information and the stored information, such as is described in the various embodiments discussed in greater detail below.

In some examples, multiple processors may be employed within the computing device 112 to generate the stimulation information received from a sensor 114. For example, each of several different frequency ranges received from a microphone may be processed by a separate processor to generate the resulting audio stimulation information. In addition, in the case of multiple sensors 114, each of these sensors 114 may be coupled with a separate processor or processors of the computing device 112 to generate the stimulation information.

The wireless transmitter or transceiver 110 may then transmit the stimulation information from the computing device 112 to the wireless receiver or transceiver 1208 coupled with the mouthpiece 101 (operation 1208). In response to receiving the stimulation information via the transceiver 1208 (operation 1210), the array controller 104 may process the received stimulation information to generate stimulation signals (operation 1212), which are then provided by way of outputs of the array controller 104 to the elements of the stimulation element array 102 to stimulate the tongue of the user (operation 1214). As with the computing device 112, the array controller 104 may employ multiple processors such that each processor is responsible for generation of some portion of the stimulation signals. For example, each processor of the array controller 104 may generate one or more of the stimulation signals for some subset of the elements of the stimulation element array 102. In other examples, each processor may be responsible for processing some portion subset of the stimulation information being received, such as a particular range of frequencies, magnitudes, time periods, and/or the like. The use of multiple processors in the array controller 104 may facilitate parallel processing multiple aspects of the stimulation information, thus potentially generating stimulation information that exhibits greater resolution, less latency, and so on.

While the operations 1202 through 1214 are shown in FIG. 12 as being performed in a particular order, other orders of performance for the operations 1202 through 1214 are also possible. For example, each of the operations, from the receiving of the sensor information (operation 1202) and stored information (operation 1204), through the providing of the stimulation signals to the stimulation element array (operation 1212), may occur on a repeating or ongoing basis. Other orders of performance of the operations 1202 through 1214, as well as the order of performance of the various method operations described below, may also be possible.

Moreover, while the various operations 1202 through 1214 are indicated in FIG. 12 as being performed either external to the mouthpiece 101 or within the environment of the mouth or mouthpiece 101, variations are also possible. For example, the receiving of sensor data from the one or more internal sensors 109, and the processing of the sensor data from the internal sensors 109 at the array controller 104, may all occur within the environment of the mouthpiece 101, possibly without any stimulation information being received via the wireless transceiver 108.

Figure 13:
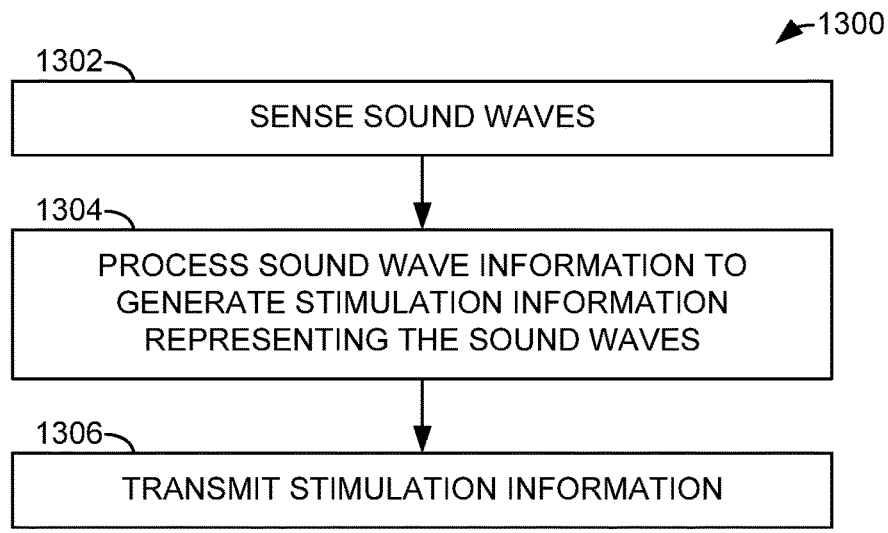
FIG. 13 is a flow diagram of an example method of stimulating the tongue using information representing sensed sound waves.

FIGS. 13-18 provide more specific examples of tongue stimulation methods that impart various types of information via the tongue to the user. FIG. 13, for example, is a flow diagram of an example method 1300 of stimulating the tongue using information representing sensed sound waves. In the method 1300, an audio sensor 114 may sense sound waves (operation 1302), such as those at the location of the user. The computing device 112 may then process information received from the audio sensor 114 (operation 1304) (e.g., information representing the sensed sound waves) to generation stimulation information representing the sound waves, and transmit the generated stimulation information via the wireless transceivers 110 and 108 (operation 1306) to the array controller 104 for generation of the stimulation signals for stimulating the tongue.

To increase the throughput of the audio content being relayed to the array controller 104, the computing device 112 may process the received audio information, such as transforming audio waveform time-domain information into frequency-domain information, such as by way of a Fast Fourier Transform (FFT) or other transformation algorithm or circuit. Such a transformation may be performed by way of hardware, software executing on a hardware processor, or some combination thereof. The resulting frequency-domain information may then be transmitted via the transceivers 110 and 108 to the array controller 104 for stimulation signal generation.

In some embodiments, one or more band-pass filters may be utilized in addition to, or in lieu of, an FFT algorithm or circuit. For example, at least one band-pass filter may be employed to filter out unwanted audio frequencies, such as, for example, frequencies beyond the hearing range of most adults. In yet other examples, the band-pass filter may be configured to filter frequencies that are not required for a particular application, such as, for example, speech recognition. In one example, the band-pass filter may be applied to the sensed audio signals prior to application of the FFT to expedite the execution of the transform. In other embodiments, a plurality of band-pass filters, each of which is tuned to pass a separate, relatively narrow band of frequencies, may be employed so that the output of each band-pass filter may closely represent a stimulation signal for each of one or more elements of the stimulation element array 102, thus potentially simplifying the generation of the stimulation information at the computing device 112 and the generation of the stimulation signals at the array controller 104. In yet other examples, each of a plurality of band-pass filters may pass a different, relatively narrow frequency band to an FFT circuit or algorithm, which may then process that particular frequency band to generate values for two or more sub-bands of the frequency band. Employing band-pass filters with an FFT is such cases may reduce the number of computations needed to generate the stimulation information to be provided to the array controller 104. Moreover, in examples in which the band-pass filters, with or without the FFT, are employed in conjunction with the audio sensor 114, the higher audio frequencies may be processed more often relative to the lower audio frequencies, thus possibly allowing faster response and/or cycle times in generating stimulation signals based on the higher frequencies of the sensed audio signals.

As discussed above, the stimulation element array 102 may include some combination of electrical, thermal, and/or chemical elements. The use of multiple stimulation technologies may facilitate the presentation of more varied or detailed information representing the sensed audio information via the user tongue. For example, different audio frequency ranges may be imparted to the tongue by different technologies (e.g. low frequencies provided by thermal stimulation elements, mid-range frequencies provided by chemical elements, and high frequencies by electrical elements). Other ways of providing different aspects of the audio information via multiple stimulation technologies are also possible.

In another example, the stimulation information being generated at the computing device 112 may represent spoken words or phrases detected in the sound waves being sensed at the audio sensor 114. For example, the computing device 112 may detect the spoken words or phrases using a speech-to-text module or application executing on the computing device 112, and then generation stimulation information that represents the spoken words or phrases. Such stimulation information, when employed by the array controller 104 to generate tongue stimulation signals, may serve as a supplement or replacement for closed captioning and similar systems. Accordingly, this stimulation information may serve as a hearing replacement for hearing-impaired individuals. In one example, the user may be trained to associate various words or sounds with particular stimulation patterns on the tongue. In some cases, such as in the onset of hearing impairment that may occur over a period of time (e.g., hearing impairment associated with neurofibromatosis type 2), the training of the user may occur while the user still retains the ability to hear words and sounds while being trained to associate those words or sounds with specific sensations on the tongue, thus possibly expediting the training process.

Figure 14:
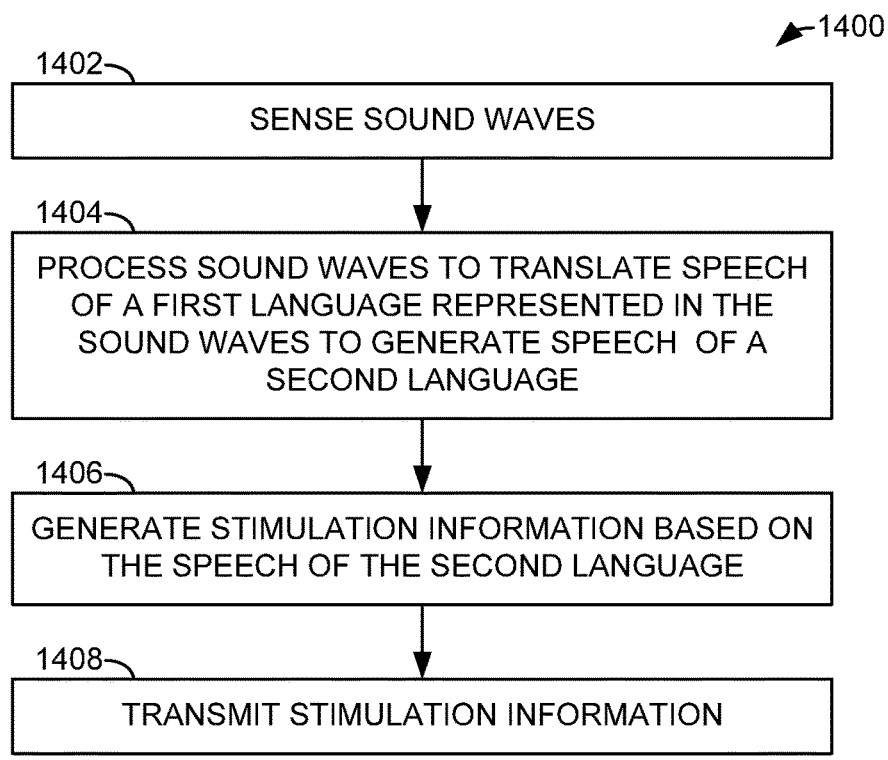
FIG. 14 is a flow diagram of an example method of stimulating the tongue using sensed sound waves to aid in learning a second spoken language.

FIG. 14 is a flow diagram of an example method 1400 of stimulating the tongue using sensed sound waves to aid in learning a second spoken language. In the method 1400, the audio sensor 114 may sense sound waves (operation 1402). The computing device 112 may then process information received from the audio sensor 114 (operation 1404) (e.g., information representing the sensed sound waves) to translate speech of a first language represented in the sound waves to generate speech of a second language (operation 1404). To accomplish this task, the computing device 112 may retrieve translation information stored at the computing device 112 or the remote computing device 116, detect the words or phrases spoken in the first language from the sounds waves (e.g., via a speech-to-text module or application executing on the computing device 112) and translate the detected words or phrases of the first language into those of the second language. The computing device 112 may then generate the stimulation information based on the translated words or phrases (operation 1406) and transmit the stimulation information to the array controller 104 (operation 1408). As with the method 1300 of FIG. 13, the array controller 104 may provide stimulation signals for electrical, thermal, and/or chemical stimulation elements based on the received stimulation information.

In this example, the first language actually being spoken may be a language unfamiliar to the user, while the second language into which the words of the first language are translated may be well-known to the user. By thus providing information representing the second language on the tongue of the user while the user hears the first language, the system 100 may provide the user with a faster, more natural way of learning a second language compared to rote memorization of vocabulary, rules of syntax, and the like.

Figure 15:
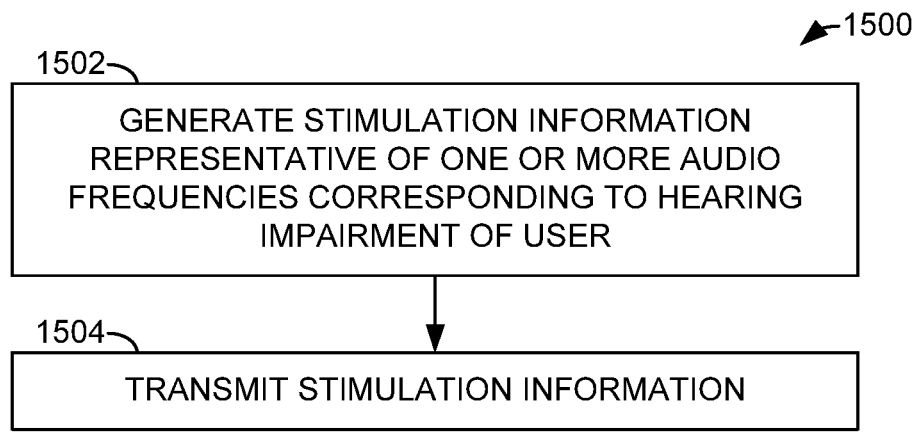
FIG. 15 is a flow diagram of an example method of stimulating the tongue as therapy for tinnitus and other hearing impairment.

FIG. 15 is a flow diagram of an example method 1500 of stimulating the tongue as therapy for tinnitus or other hearing impairments. In the method 1500, the computing device 112 may generate stimulation information representative of one or more audio frequencies corresponding to a hearing impairment of the user (operation 1502) and transmit the stimulation information to the array controller 104 (operation 1504) for subsequent generation of the stimulation signals for electrical, thermal, and/or chemical stimulation elements. For example, the stimulation information may be based on some knowledge or identification of the problematic audio frequencies associated with a hearing impairment, such as tinnitus, experienced by the user, as well as on proposed stimulation information that may serve as therapy for the impairment at those audio frequencies. For example, in at least some cases, tinnitus is experienced by a user as an audible ringing at one or more particular frequencies of hearing impairment of the user. As the components of the ear are not detecting sounds at those frequencies, the ear of the user may react by providing those particular audio frequencies to the brain on an ongoing basis. However, by providing tongue stimulation at the affected frequencies, the brain of the user may react by ignoring the signals being provided by the ear at those frequencies, thus potentially reducing the effects of the tinnitus experienced by the user.

Figure 16:
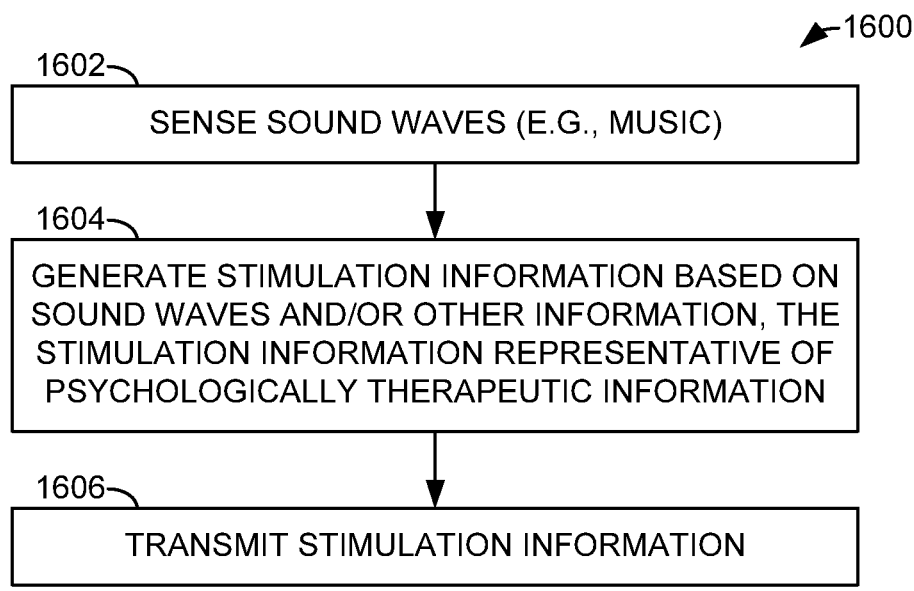
FIG. 16 is a flow diagram of an example method of stimulating the tongue as therapy for a psychological condition.

FIG. 16 is a flow diagram of an example method 1600 of stimulating the tongue as therapy for various psychological conditions. In one example of the method 1600, the audio sensor 1400 may sense sound waves, such as, for example, those associated with the playing of music (operation 1602). The computing device 112 may generate stimulation information based on the sound waves (operation 1604) and transmit the generated stimulation information via the transceivers 210 and 208 to the array controller 104 (operation 1606) to generate stimulation signals for electrical, thermal, and/or chemical stimulation elements. In this example, the stimulation information may serve as therapeutic information used as a treatment for anxiety, depression, and other psychological issues. More specifically, the stimulation information, when used to stimulate the tongue, may act to "normalize" otherwise irregular brainwave patterns that may cause anxiety, depression, and the like, much in the way that listening to music, manually tracing lines, and performing other activities or experiencing other sensations affects the brain of the user. Instead of basing the generated stimulation information on audio waves, the computing device 112 may retrieve preexisting stimulation information from local or remote data storage, or from the remote computing device 118, that are devised to provide a user some therapeutic benefit.

In other examples, the stimulation information based on the sensed sound waves of music may be intended primarily to enhance the enjoyment of the music by the user. For example, the stimulation information may be intended to provide a gentle or pleasing sensation to the tongue during quiet musical passages, generate a more intense sensation during loud or fast musical sections, and so on.

Figure 17:
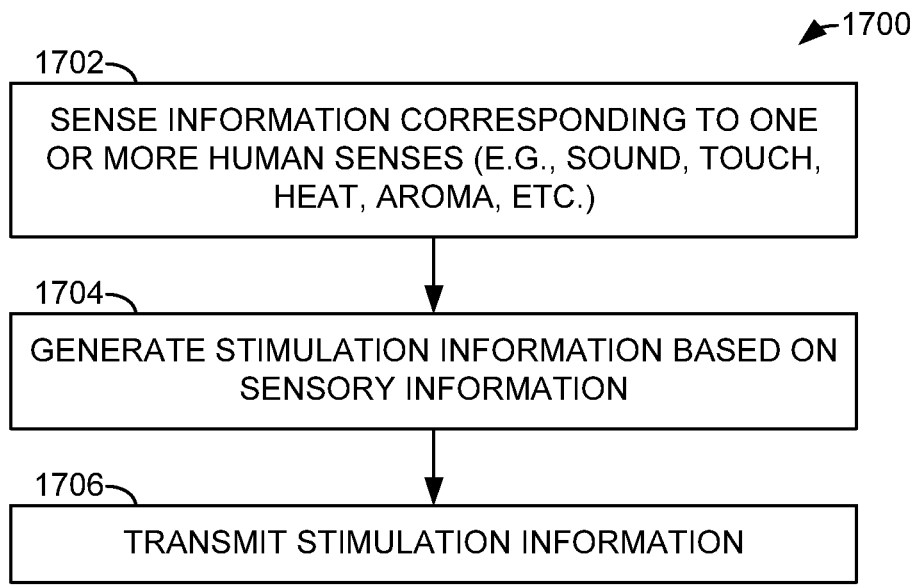
FIG. 17 is a flow diagram of an example method of stimulating the tongue to map one or more types of sensory information to the tongue.

FIG. 17 is a flow diagram of an example method 1700 of stimulating the tongue to map one or more types of sensory information to the tongue. In the method 1700, one or more sensors 114 may sense information relating to one or more human senses (e.g. sound, touch, pressure, heat, cold, aroma, etc.) (operation 1702). In some examples, one or more internal sensors 109 may be employed to provide sense information as well. The computing device 112 may then generate stimulation information based on the received sensory information (operation 1704) and transmit the generated stimulation information to the array controller 104 (operation 1706) for generation of stimulation signals for electrical, thermal, and/or chemical stimulation elements. In some example, sensory information from the internal sensors 109 may be received and processed at the array controller 104 without the involvement of the computing device 112, or such sensory information may be transmitted to the computing device 112 via the array controller 104 and the transceivers 108 and 110 for generation of the stimulation information.

In some embodiments, employing the method 1700 of FIG. 17 may allow the user to receive sensory information that may otherwise be masked or diminished by other sensory information. For example, information at certain audio frequencies, such as at extremely low or high audible frequencies, may be masked by strong simultaneous mid-range audio frequencies. Such frequencies may be provided to the user via tongue stimulation so that the user may experience those otherwise "lost" frequencies. Similarly, supersonic or subsonic frequencies outside the normal hearing range of the user may also be mapped to the tongue. Generating such stimulation information may also include touch information to enhance the sensory capabilities of a surgeon, light or image information (e.g., infrared information) for navigation or searching operations, and the like. In addition, the additional information, such as additional audio information, may be provided via tongue stimulation for therapeutic or recreational purposes.

In yet other embodiments, one or more of the sensors 114 may sense physical, electrical, magnetic, chemical, or other aspects of a particular environment that are not related to human sensory capabilities. For example, the one or more sensors 114 may include chemical sensors, electromagnetic wave/field sensors, and/or so on to detect various conditions. The computing device 112 may then generate stimulation information indicative of the information received via such sensors 114, which is ultimately reflected in the stimulation signals provided to the stimulation elements, thus relaying that information to the user.

Figure 18:
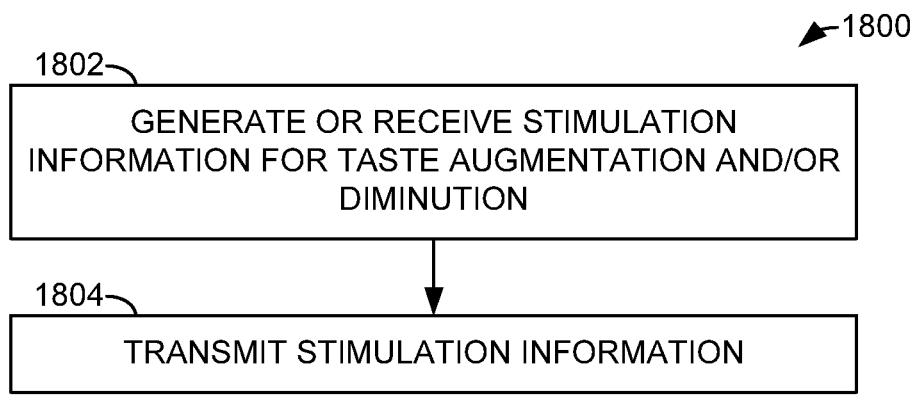
FIG. 18 is a flow diagram of an example method of stimulating the tongue to facilitate augmentation or diminution of taste, such as during consumption of food or medication.

FIG. 18 is a flow diagram of an example method 1800 of stimulating the tongue to facilitate augmentation or diminution of taste, such as during consumption of food. In an embodiment of the method 1800, the computing device 112 may generate or receive stimulation information that would tend to augment or diminish the ability of one or more areas of the user's tongue to sense particular types of tastes (e.g., sour, sweet, salty, spicy, etc.) (operation 1802), and then transmit the stimulation information to the array controller 104 for the generation of corresponding stimulation signals for the stimulation elements. In one example, the stimulation elements may include chemical stimulation elements that produce chemicals or pH levels that affect the tasting ability of taste buds. In other examples, electrical and/or thermal stimulation elements may also be employed to augment or mask the operation of the taste buds. In one embodiment, the user may possess a reduced ability to taste at least certain types of foods. Under this scenario, the computing device 112 may generate stimulation information to enhance certain taste buds responsible for the types of tastes that the user lacks. In another situation, the food being consumed by a user, such as what may be encountered as part of a prescribed diet (e.g., for weight control, management of cholesterol or blood pressure), may be bland, tasteless, or even unpalatable (e.g., extremely bitter or sour). To render such food more enjoyable, the computing device 112 may generate stimulation information to enhance any pleasant tastes that may be provided by the food, and/or mask or replace any unpalatable aspects of the food. In other examples, some types of medications, such as steroids used for autoimmune disease suppression, may be extremely bitter or sour. Providing stimulation information that would counteract such bitterness or sourness may thus allow the user, such as a child, to consume the medication more easily.

In another example, the internal sensors 109 may include chemical sensors that determine chemicals that may be present in the saliva of the user. The array controller 104 or the computing device 112 may then receive sensor information from the internal sensors 109 and generate stimulation information based on the sensor information to interact with the saliva at various locations on the tongue to enhance or diminish various tastes.

Figure 19:
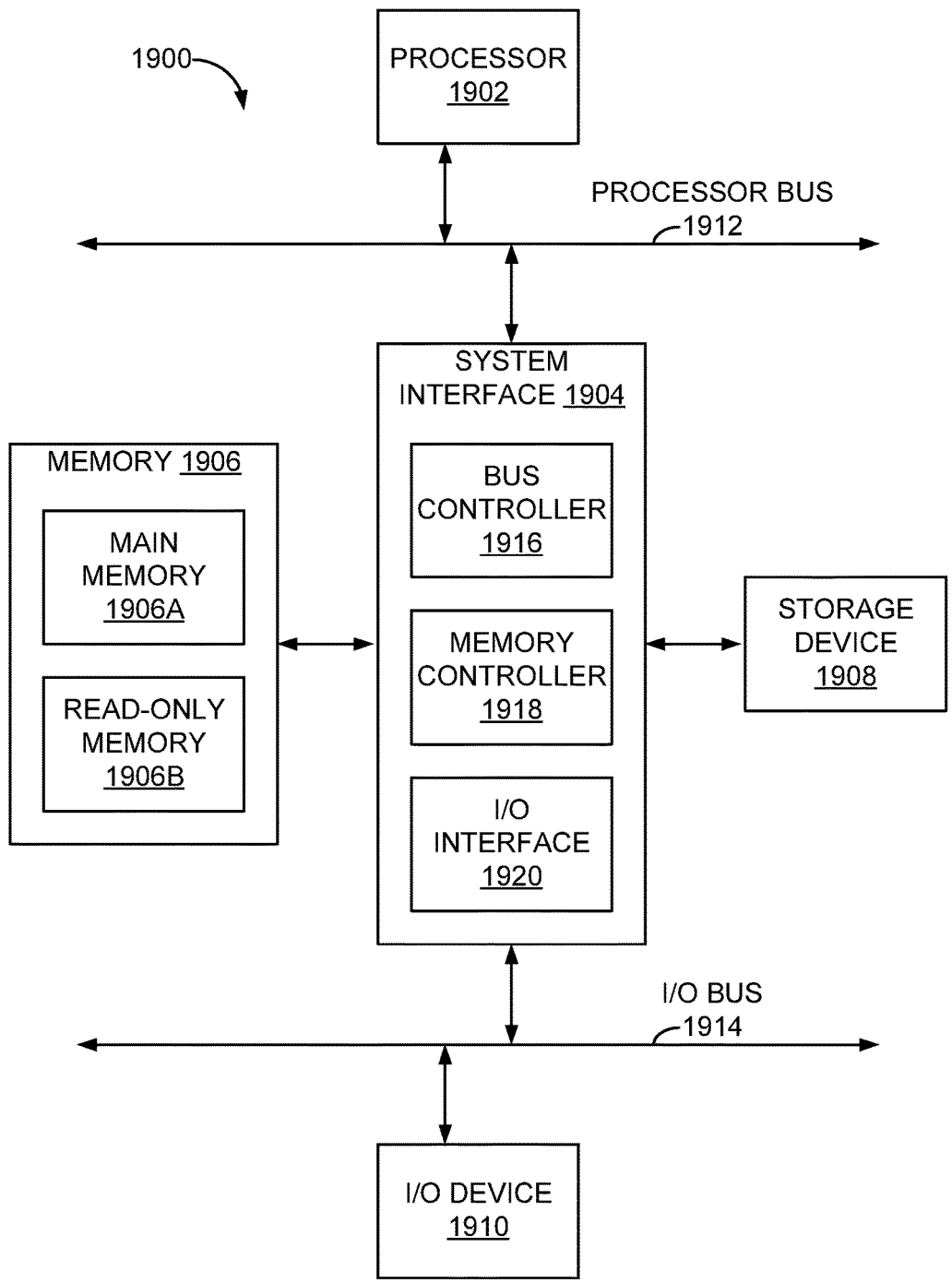
FIG. 19 is a block diagram illustrating an example of a computing device or computer system that may be employed to implement the embodiments described herein.

FIG. 19 is a block diagram illustrating an example of a computing device or computer system 1900 which may be used to implement the embodiments disclosed above, such as the array controller 104, the computing device 112, and/or the remote computing device 118 of FIG. 1. Embodiments disclosed herein include various operations that maybe performed by hardware modules or components, or hardware modules or components used in combination with software instructions. Moreover, as described herein, in some embodiments, a first module or component may be hardware that is programmed by one set of software or firmware instructions to perform one or more functions, while a second module or component may be that same hardware that is programmed by another set of software or firmware instructions to perform one or more other functions. As a result, the same hardware may represent the first module during one period of time, and may represent the second module during the same time or a second period of time. According to one example, the computing device or system 1900 may include at least one processor 1902, at least one system interface 1904, at least one memory 1906, at least one storage device 1908, and at least one I/O device 1910. The at least one I/O device 1910 may include transmitters, receivers, or transmitters for transmitting information wireless, as well as sensors for sensing sounds, light, and other sensations. The system 1900 may further include at least one processor bus 1912 and/or at least one input/output (I/O) bus 1914.

The processor 1902 may include one or more internal levels of cache (not shown in FIG. 19) and can be any known processor, such as a microprocessor, microcontroller, digital signal processor, graphics processor, or the like. The processor bus 1912, also possibly known as a host bus or a front side bus, may be used to couple the processor 1902 with the system interface 1904. The system interface 1904 may be connected to the processor bus 1912 to interface various components of the system with the processor 1902. System interface 1904 may, for example, include a bus controller 1916 or bus interface unit to direct interaction with the processor bus 1912 and a memory controller 1918 for interfacing the memory 1906 with the processor bus 1912. The system interface 1904 may also include an I/O interface 1920 to interface one or more I/O devices 1910 with the processor 1902.

The memory 1906 may include one or more memory cards and control circuits (not depicted in FIG. 19). The memory 1906 may include a main memory 1906A and/or a read-only memory (ROM) 1906B. The main memory 1906A can be random access memory (RAM) or any other dynamic storage device(s) for storing information and instructions to be executed by the processor 1902. Main memory 1906A may be used for storing temporary variables or other intermediate information during execution of instructions by the processor 1902. The read-only memory 19068 can be any static storage device(s), such as Programmable Read Only Memory (PROM) chip for storing static information and instructions for the processor.

According to one embodiment, the above methods may be performed by the computer system 1900 in response to the processor 1902 executing one or more sequences of one or more instructions contained in the main memory 1906A. These instructions may be read into main memory 1906A from another machine-readable medium capable of storing or transmitting information in a form (e.g., software, processing application) readable by a machine (e.g., a computer). Execution of the sequences of instructions contained in the main memory 1906A may cause the processor 1902 to perform the process operations described herein.

A machine-readable media may take the form of, but is not limited to, non-volatile media and volatile media. Non-volatile media may include a mass storage device 1908 and volatile media may include dynamic storage devices. Common forms of machine-readable media may include, but are not limited to, magnetic storage media (e.g. hard disk drive); optical storage media (e.g. Compact Disc Read-Only Memory (CD-ROM) and Digital Versatile Disc Read-Only Memory (DVD-ROM)), magneto-optical storage media; read-only memory (ROM); random access memory (RAM, such as static RAM (SRAM) and dynamic RAM (DRAM)); erasable programmable memory (e.g., erasable programmable read-only memory (EPROM) and electrically erasable programmable read-only memory (EEPROM)); flash memory; or other types of media suitable for storing computer or processor instructions.

As discussed above with reference to FIGS. 11-18, the stimulation element array 102 discussed herein may be configured to perform lingual nerve mapping or perception mapping experiments on a user or multiple users to determine some optimum location for the electrical, thermal, and/or chemical stimulation elements to be used, as well as other characteristics of the stimulation element array 102 and the array controller 104. For example, the array controller 104 or the computing device 112 may be configured to generate series or sets of predetermined stimulation signals to determine sensitivity with respect to electrical, thermal, and/or chemical stimuli at various areas of the tongue. One particular embodiment of the lingual nerve mapping or perception mapping procedure is now described to map perceived intensity and two-point (or more) discrimination ability for lingual stimulation. The results of the mapping may then be utilized to improve the information provided to a subject through the stimulation element array 102 device described above.

In general, the testing described below is designed to determine how the positions of active electrodes affect perceived intensity and discrimination of stimulation on different subjects. In one specific testing procedure, the testing is conducted to show: (1) Whether specific 1 cm$^2$ regions of the tongue of the subject are more sensitive to electro-tactile or other types of stimulation relative to other regions; (2) Whether specific 1 cm$^2$ regions of the tongue of the subject are better able to discriminate two active electrodes presented at a constant voltage relative to other regions; (3) Whether closely spaced electrodes are perceived as more intense than those that are spaced further apart; and (4) Whether the orientation of 2 active electrodes or other stimulators affects perceived intensity or discrimination ability. Through this information, a patient-specific lingual sensitivity map is generated that may then be used to generate a patient-specific application of the stimuli of a stimulation element array 102 device.

Figure 20:
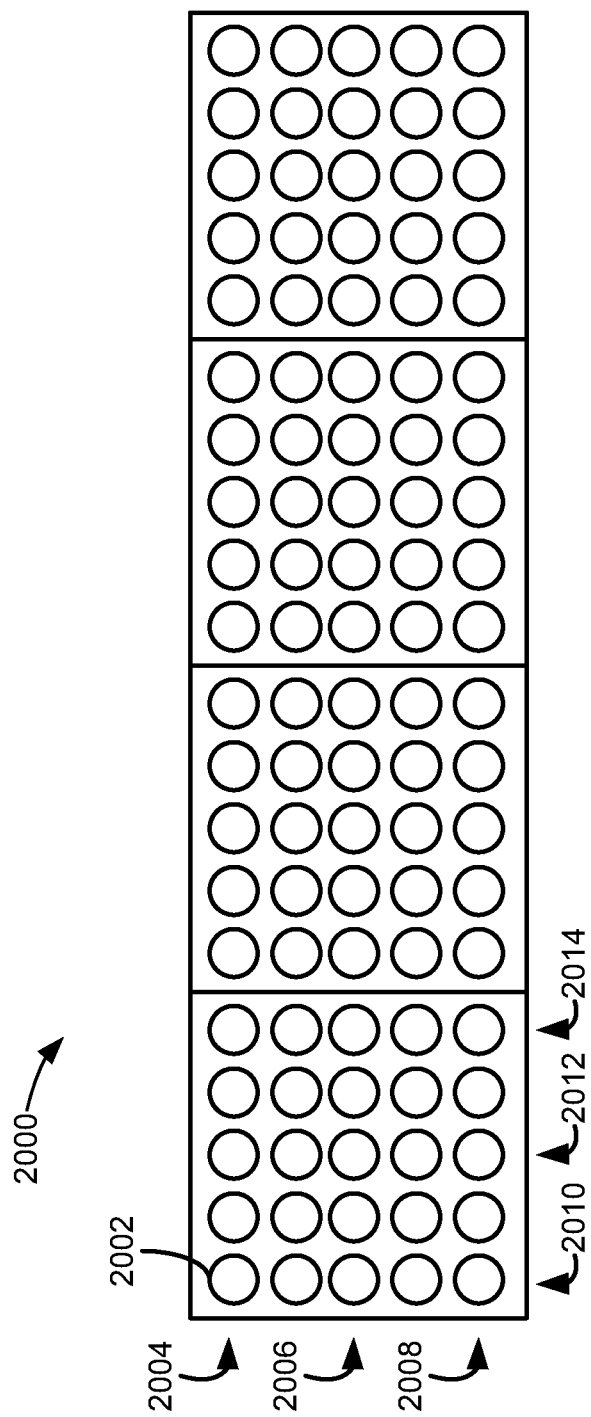
FIG. 20 is an illustration of a rectangular array of stimulation elements, divided into four sub-arrays, for testing a two-point discrimination ability of a subject.

To begin the testing procedure, a pattern of signals are applied to a stimulation device placed on the subject tongue, such as the mouthpiece 101 including the stimulation element array 102 discussed above. In one particular embodiment, a simulation array 102 may include a 5×20 rectangular array, divided into four 5×5 sub-arrays, as illustrated in FIG. 20. The 5×20 array 2000 has 2 mm center-to-center spacing (approximately 1 mm edge-to-edge). The completed array measured 1 cm by 4 cm and could be placed on any number of locations along the tongue. In a particular embodiment, the testing included placement of the array 2000 on 4 distinct areas of the tongue, resulting in coverage of a 4 cm$^2$ region of the anterior tongue.

Figure 21:
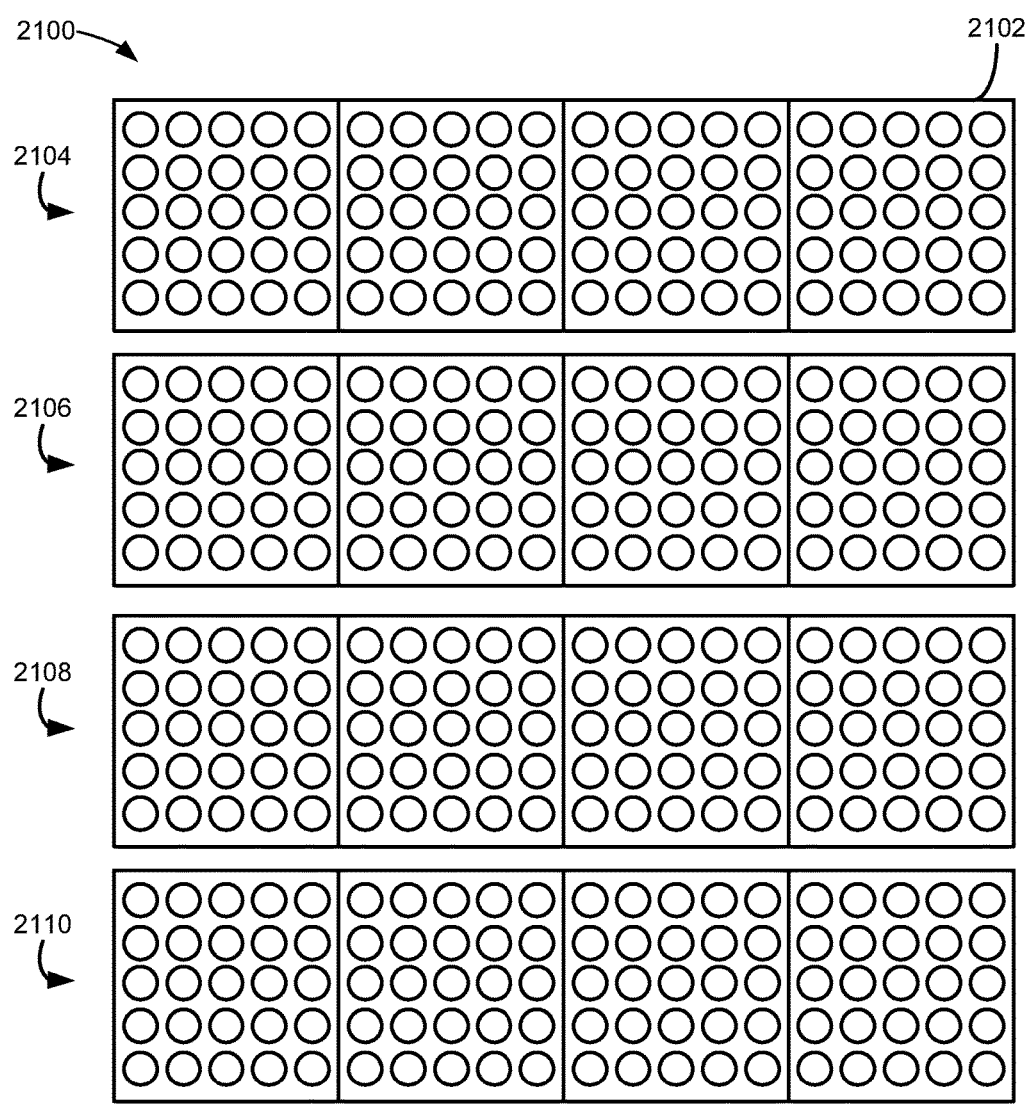
FIG. 21 is an illustration of utilizing the rectangular array of stimulation elements of FIG. 20 in four locations to test a larger portion of the subject's tongue.

A graphic representation of the array as a 4 cm$^2$ region is illustrated in the upper-right of FIG. 21. As shown, the complete array 2102 includes a first set of a 5×20 array 2104 in a first location on the tongue. A second placement of the 5×20 array 2106 may be used to apply stimulation to a second location on the tongue. Thus, the 5×20 array 2104 may be placed on the tongue in a first location and testing may occur as described herein. The 5×20 array may then be moved on the tongue to a second location 2106 to apply the stimulation test on the second location. A third location 2108 and a fourth location 2110 may also be utilized to conduct the testing by moving the 5×20 array to those locations for testing. In this manner, a complete 4 cm$^2$ region of the tongue of the participant may be tested.

Although the particular simulation array 102 of FIG. 20 and FIG. 21 is discussed, it should be appreciated that any type of stimulation array may be used during testing to stimulate any portion of the subject's tongue. For example, a complete 20×20 array (such as that illustrated in the upper right corner of FIG. 21) may be constructed and used during testing such that movement of the array is not required during testing to test various locations of the tongue. In general, the stimulation element array used for testing may be any shape and size and may include any number of stimulation elements arranged in any pattern.

In one particular testing procedure, 3 rows and 3 columns of electrodes were selected in each 5×5 sub-array to be activated during the testing. As shown in FIG. 20, the top row 2004 of the sub-array, the middle row 2006, and the bottom row 2008 are selected to be activated in a particular pattern. First column of stimulation elements 2010, middle column 2012, and last column 2014 may also be activated. In each row and each column, 4 pairs of electrodes that are 8, 6, 4, or 2 mm center to center apart are utilized. For example, FIG. 21 illustrates the activation of the stimulation elements to conduct the two-point discrimination testing of the participant for elements that are 8 mm apart. In general, however, each of the 16 sub arrays may be tested for 2, 4, 6, and 8 mm discrimination ability in each of the 3 rows and 3 columns in the sub-array.

In one particular implementation, the 4 pairs of electrodes that are spaced 8, 6, 4, or 2 mm center to center apart are randomized in a list and mixed with another list of 20 random, single electrodes, providing 116 stimulus patterns. A list of the 116 stimulus patterns is generated and randomized for each of the 4 positions in which the array could be positioned in the mouth. Through the application of the list of stimulus patterns, each of the 16 sub-arrays shown in FIG. 21 is tested for 2, 4, 6, and 8 mm discrimination ability in each of the 3 rows and 3 columns in the sub-array. Thus, 464 separate patterns across a 4 cm by 4 cm area of each participant's tongue (384 of these patterns were from two point discrimination tests, and the remaining 80 were single electrode stimulus at random locations) is applied to the participants tongue in this particular implementation. It should be appreciated, however, that any pattern of activating the stimulators in an array may be utilized during testing.

In one implementation, the stimulus elements provide an electrical stimulus to the tongue, as described in greater detail above. Activation of the electro-stimulus may include a constant value of 5 volts for pulse amplitude, an Outer Burst Period (OBP) of 36 ms, an Inner Burst Number (IBN) of 3, a Peak to Peak (PP) length of 10 μs, and an Inner Burst Period (IBP) of 150 μs. Pulse Width (PW), and Outer Burst Number (OBN) correlate with effective perception and comfort of the stimulus. However, the electronic signal may include any parameters as determined by the participant or a test administrator to obtain the desired two-point discrimination along the tongue. For other stimulus element types (such as chemical or thermal), stimulation settings may be selected by the participant or administrator to enhance the detectability of the application of the stimulus as desired.

One goal of the above-described testing is to determine how many stimuli and the location of such stimuli that may be placed on an array on the tongue so that each stimulus on the array produces a distinct sensation and "simultaneously" active stimuli do not perceptually interact with each other. In the particular example of electrical stimuli, simultaneously active electrodes are not actually active at the same time due to the waveform structure described above, but sensations from these electrodes are perceived to be simultaneous due to the small time parameters of the waveform. In essence, to ensure distinct sensations, the distance between adjacent stimuli elements may be sufficiently large so that nerve fibers stimulated by one stimulus element are not stimulated by adjacent stimulus elements.

Through the testing described above, the smallest tested distance for which a participant could discern two distinct sensations was determined for both horizontally and vertically oriented electrodes on 48 loci for a participant. For loci on the tongue where two distinct sensations could not be distinguished at the maximal 8 mm separation, the two-point discrimination distance may be assumed as 1 cm. Distances between loci varied from 2 mm to 10 mm and values between loci may be interpolated on a grid with 2 mm spacing using an iterative method. This data is then used to calculate the dimensions of a rectangle at each point that would contain the receptive fields activated by a stimulus element placed at its center. From this calculation, the total number of stimulus elements that could be placed on the 4 cm by 4 cm tested area of the tongue without influencing the perception of adjacent stimuli is then calculated for each participant undergoing the described test.

Figure 22:
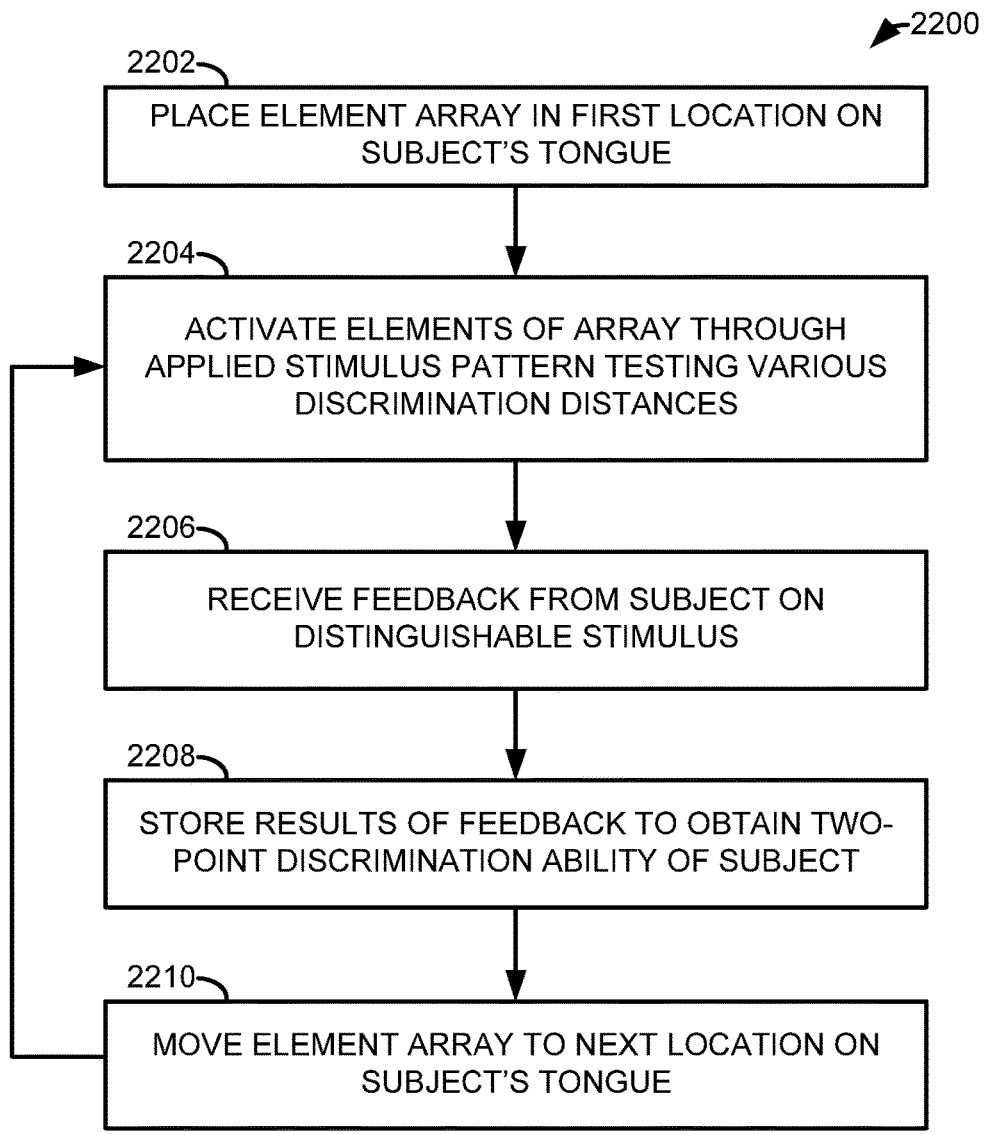
FIG. 22 is a flowchart of a method for conducting a two-point discrimination test of a tongue of a participant of stimulus elements applied to the tongue.

FIG. 22 is a flowchart of a method 2200 for conducting a two-point discrimination test of a tongue of a participant of stimulus elements applied to the tongue. One or more of the operations of the method 2200 may be performed by an administrative or testing device to determine a two-point discrimination map of a participant or subject of the test. Beginning in operation 2202, a stimulation element array device 102 (such as that discussed above) including any number of stimulation elements may be placed in a first location adjacent or upon the participant's tongue. In one embodiment, the stimulation elements are electrodes configured to provide an electrical stimulation to the participant's tongue. In other embodiments, the stimulation elements may be chemical or thermal elements, as described.

In operation 2204, at least two stimulation elements are activated through one or more patterns to test various discrimination distances between the stimulation elements. For example, two or more stimulation elements may be activated at distances of 2, 4, 6, and 8 mm within the stimulation element array. In general, any number of stimulation elements may be activated in any pattern to test the participant's ability to distinguish between the two or more stimulation elements. During the application of the stimulation pattern, the testing device or administrator receives feedback from the participant indicating that the participant can distinguish the application of the two or more stimulation elements or if the participant experiences the sensation of a single stimulation element in operation 2206. In one example, the participant may provide an indication of two, distinguishable sensations on the tongue through a feedback mechanism or device during application of any of the stimulation elements.

In operation 2208, the results of the feedback by the participant are stored in some form (such as a spreadsheet or table of the particular stimulation element patterns that the participant could distinguish as distinct stimuli) from which a particular mapping of the participant's two-point discrimination sensitivity may be determined. In one example, the results of the testing are entered into a database stored in a computer-readable medium for translation into a sensitivity map of the participant's tongue, described in more detail below. In some instances, the results of the participant's test may be broken up into various regions of the tongue to further understand the two-point discrimination sensitivity of the participant's tongue.

In operation 2210, the element array is moved to a second location (such as adjacent the first location on the participant's tongue) and the testing at the second location occurs by returning to operation 2204. In this manner, several locations on the participant's tongue may be tested to obtain a two-point discrimination database of the particular participant under test for use in determining a sensitivity map of the participant.

The ability to generate a two-point discrimination map of a particular participant or patient may improve the ability of a tongue stimulation device to provide or convey information to the patient. For example, recent research indicates that sensitivity and discrimination ability varies considerably across the surface of the tongue and between participants, indicating that the efficacy of tongue stimulation devices can be drastically improved by designing devices specific to the perceptual ability of individual users. Thus, using data from lingual perception tests, such as the two-point discrimination tests described above, to design individual stimulation arrays for stimulating the tongue of a user may improve the efficiency of such devices.

Figure 23:
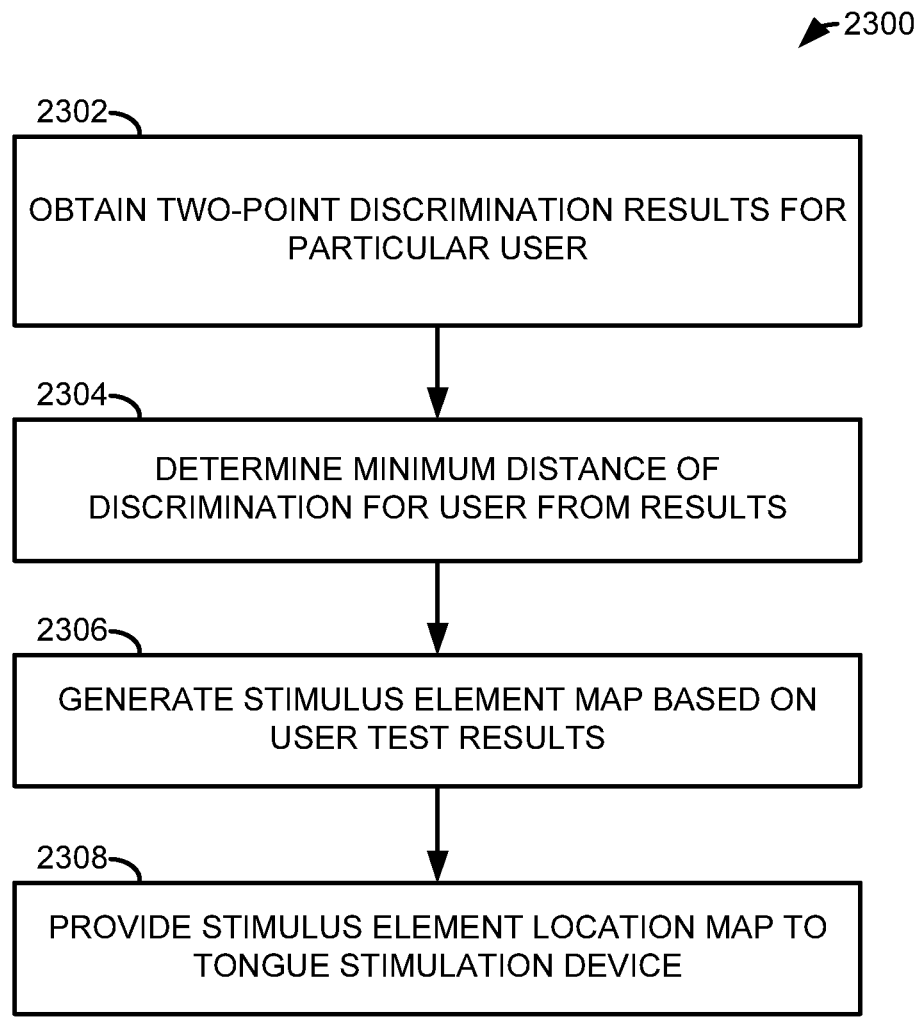
FIG. 23 is a flowchart of a method for providing stimulus to a subject's tongue based on a stimulus location map generated for the subject.

Tongue stimulation devices would improve substantially if individual variability was assessed and used to create an individualized approach to sensory substitution similar to the use of vision tests or hearing tests to determine individual needs for corrective lenses or hearing aids. As such, methods are discussed herein to apply two-point discrimination results information from the testing described above for a particular participant to a stimulation element array map that customizes the array to the participant to improve the efficacy of information provided through a tongue stimulation device. In particular, FIG. 23 illustrates a flowchart of a method 2300 for utilizing the results of a two-point discrimination test on a tongue of a particular subject to apply information through a stimulation element array of a tongue stimulation device. In one embodiment, the operations of the method 2300 are executed by a control system of a tongue stimulation device, such as computing device 112 of the tongue stimulation system 100 described above with relation to FIG. 1.

Beginning in operation 2302, the control system obtains two-point discrimination results for a particular subject from a two-point discrimination test applied to the tongue of the subject. As explained above, the two-point discrimination test may determine a minimum distance between two stimulus elements on a stimulation element array of a tongue stimulation device that the subject may detect on the tongue. This results information may be stored in a database accessible by the control system and in a format (such as a spreadsheet or list) from which the control system may obtain or calculate a minimum distance between any two stimulation elements on the array that the subject may distinguish as unique or separate stimuli.

In operation 2304, the control system determines the minimum distance between any two stimulation elements on the array that the subject may distinguish as unique or separate stimuli. In other words, the distance at which the particular subject can distinguish stimuli applied from two stimulus elements of the array are noted or calculated by the control system. The distance may be a vertical distance between the elements, a horizontal distance, or a combination of both a vertical distance and a horizontal distance along the array of stimulation elements.

Figure 24:
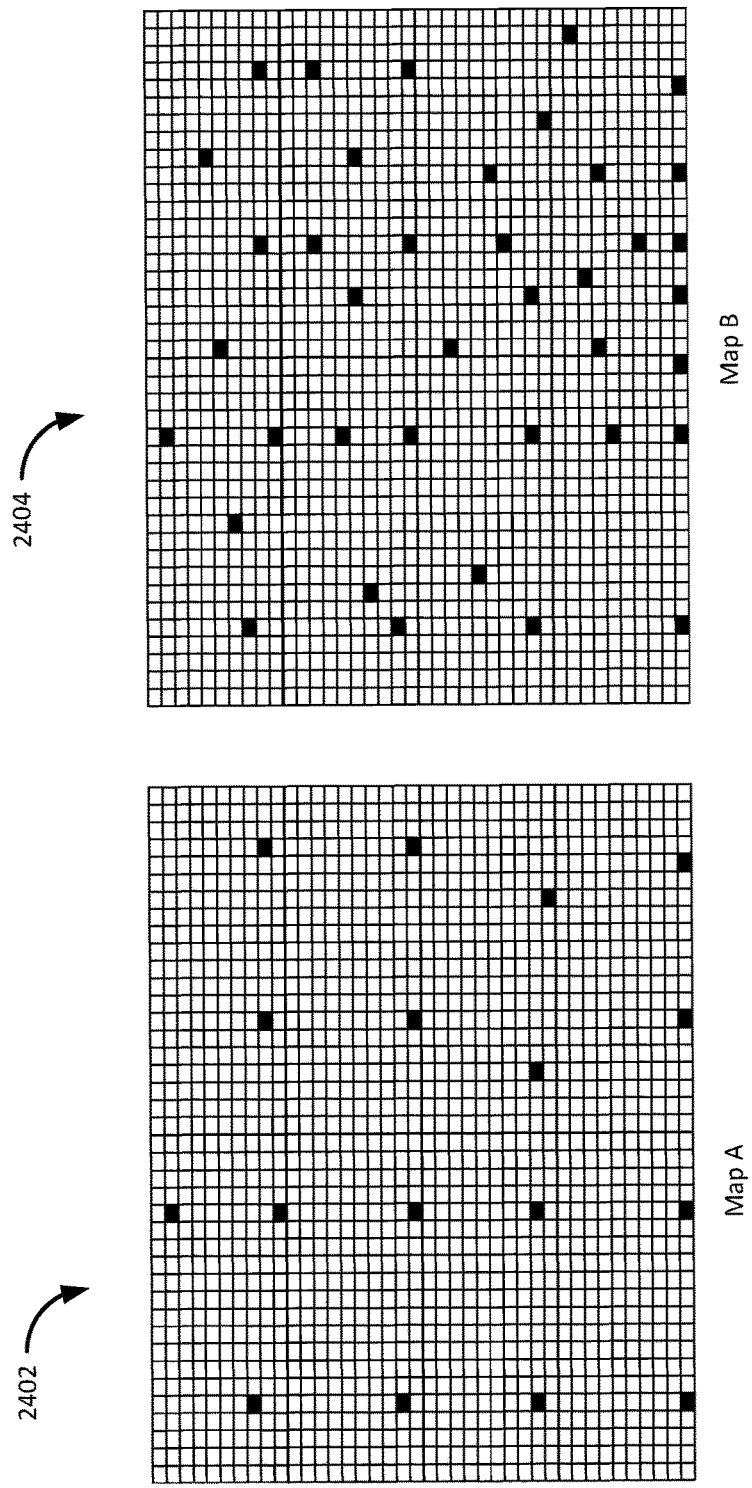
FIG. 24 is an illustration of two stimulation element array maps generated for two different study participants utilizing results from a two-point distinction testing.

With the calculated minimum distance between elements of the element array at which the particular subject can detect distinct stimuli from the stimulation elements, the control system may generate an individual stimulation element array map for the particular subject. In particular, FIG. 24 illustrates two stimulation element array map generated for two different study participants using the results from the two-point distinction testing for the two participants. The two maps 2402, 2404 illustrate an area of 4 cm by 4 cm of the respective subject. Map A 2402 provides a relative stimulus element location for a first participant and Map B 2404 provides a relative stimulus element location for a second participant. Each square of the maps 2402, 2404 illustrate a 1 mm by 1 mm area of the participant's tongue, with locations of stimulus elements of the corresponding stimulus element array illustrated as black squares. In the maps 2402, 2404 illustrated, the anterior region of the tongue (tip of tongue) is oriented down in the images, with left and right sides of the tongue corresponding to the left and right side, although the maps may be oriented in any manner.

As can be understood from the placement of the stimulus elements in the respective maps 2404, 2404 of the different participants of the test, the participant corresponding to map A 2402 had much poorer two-point discrimination ability than the participant corresponding to map B 2404. As such, fewer stimulus elements spaced further apart are located in the map 2402 for the first participant. In particular, the element array 2402 for the first participant uses 17 stimulus elements, while the array 2404 for the second participant uses 39 stimulus elements. In some instances, the number of stimulus elements on individual stimulus elements arrays may range by a factor of 6 between participants.

In one particular embodiment, the stimulus element maps for a user may be generated through an iterative process. For example, a computer program may execute a method to locate a first stimulus element at some location on the tongue stimulation device as it corresponds to a location of the user's tongue. The method may then reference a vertical and horizontal discrimination ability of the user's tongue at the point of the electrode initial placement. The method may then place another electrode a horizontal distance, a vertical distance, or a combination of both horizontal and vertical distances according to the respective discrimination ability in that direction of the user. This general process may be repeated as often as desired to locate each of the stimulus elements in the element array for that particular user. The initial location and distance directions from the starting point may be varied during the iterative process. 'Tight-pack' or 'close-fit' algorithms may be implemented with the goal of maximizing the number of electrodes or other stimulation elements that can be placed adjacent a person's tongue on the stimulation device. In yet another embodiment, multiple placement programs or methods may be utilized to each generate an array of stimulus elements, with the process with the largest number of placed electrodes for an individual selected. It should be appreciated, however, that any process may be utilized to locate the stimulus elements on the tongue stimulation device, including non-iterative methods. A similar technique could be used to achieve the opposite goal, such as if distinct discreet sensations through the tongue are undesirable for an application.

The particular stimulus element map for a subject or patient may be utilized by the control system to provide information to the patient through the activation of one or more of the identified stimulus elements in operation 2308. The activation of the stimulus elements is described above. However, the selection of which stimulus elements to activate may be based on the personal stimulus element map generated for a particular subject. For example, activation of the stimulus elements illustrated in Map A 2402 may provide information to the user whose test results determined the placement of the elements in Map A. Similarly, activation of the stimulus elements illustrated in Map B 2404 may provide information to the user whose test results determined the placement of the elements in Map B. As should be appreciated, a higher granularity of information may be provided to the user of Map B 2404 as the user may distinguish more stimulus elements separately when compared to the user of Map A 2402. By tailoring the particular stimulation elements utilized (or the relative position of the utilized stimulation elements on a tongue stimulation device) based on the particular subject's two-point discrimination ability, the efficacy of providing information to the subject may be improved over a simple standard application of stimulus elements.

The personalized stimulation element map illustrated in FIG. 24 may be utilized to provide stimulation to the participant's tongue. In particular, a tongue stimulation mouthpiece device may be controlled or constructed with the personal mapping information obtained above to provide a personal interaction with the tongue stimulation device for the particular participant. For example, the tongue stimulation device discussed above with reference to FIGS. 2A and 2B may include a mouthpiece 101 with an array of stimulation elements 102. Activation of the stimulation elements 202 of the array 102 may be controlled by a tongue stimulation system. Thus, the control system may determine particular elements 202 within the array 102 to activate and provide stimulation of some kind to the patient's tongue such that not all of the elements 202 of the array 102 are activated at once. To determine which of the elements 202 to activate, the control system may utilize the stimulation map generated for the particular user. In other words, the control system may utilize the generated stimulation element map for the user to activate certain elements 202 of the array of elements 102 to provide stimulation to the user's tongue, while not activating others at the same time. This may preserve the two-point discrimination of the stimulation by the user while maximizing or improving the bandwidth of information that may be provided to the user at any one time.

In another embodiment, the user-specific generated map may be utilized to create or construct a personal tongue stimulation device. In this embodiment, stimulation elements 202 may be disposed on the mouthpiece 101 in the areas or placement defined in the stimulation element map generated for the user. Areas of the tongue on which the user cannot distinguish two separate stimulations may not include stimulation elements 202, or may simply have stimulation elements that are not active. Thus, rather than configuring the operation of a generic tongue stimulation device, a personal tongue stimulation device may be created from the user-specific stimulation element map determined from the testing of the user discussed above.

The information obtained from the two-point discrimination testing described above may also be used to further enhance the efficacy of a tongue stimulation device in providing information to a user of the device. For example, the results of the testing may be utilized to modify audio and language encoding to enhance information transfer of the device. Data from the perceptual tests described above can be analyzed to identify the rate and complexity of information that can be effectively communicated to participants using lingual stimulation. Though the ability of a user to perceive and process information from lingual stimulus likely improves with training, matching the presentation rate of information to the perceptual abilities of the user so that the device is immediately helpful may create improved effectiveness of the device from the initial application.

As discussed above, the user-specific stimulation element map may be generated through a series of testing that determines a user's ability to distinguish between two stimuli applied to the user's tongue. However, in another implementation, the user-specific stimulation element map may be generated through an analysis of the visible fungiform papillae density on the user's tongue. In particular, preliminary research suggests that visible fungiform papillae density on the tongue correlates to local perceptual ability. In one embodiment of the present disclosure, a photograph taken of a user's tongue may be analyzed, either by a technician or through one or more image processing algorithms, to automatically identify regional papillae density of a participant's tongue. Data suggests that there is a correlation between fungiform papillae density and the discriminatory ability of the tongue, indicating that somatosensory fibers are concentrated in papillae. Thus, the control system of the tongue stimulation device may be configured to analyze and identify fungiform papillae of a particular subject's tongue and calculate density of papillae using a digital image of the tongue surface. This information obtained through the analysis of the photograph of the user's tongue may then be utilized to create the stimulation element map for the user. The user map may then be used to create a custom stimulation device as described above.

The photograph utilized to determine the location of the taste buds or papillae of the subject may be both visible photography and non-visible photography. For example, a visible (at least to a human observer) photograph of the tongue may be obtained and the taste buds or papillae may be visibly counted to determine the density and location of such features. The use of a dye or other mechanism and the placing of a pre-cut strip of paper on the tongue for size reference to further enhance the appearance of the papillae or taste buds may be used during this procedure. In another example, an infrared or ultraviolet image (or other non-visible photograph) of the subject's tongue may be obtained and analyzed to determine the location of the taste buds on the subject's tongue. The non-visible photography may provide additional indicia of the location and density of the taste buds of the user, such as blood flow or other non-visible indicia.

In one implementation, the mapping of the discriminatory ability and sensitivity of a participant may include utilizing the tongue stimulation device to sense a location of the tongue against the body of the device or otherwise sense which stimulation elements are in contact with the tongue. This location sensing may be useful for detecting the edge of a subject's tongue while mapping their perceptual ability to generate the stimulus location maps discussed above. In particular, sensing the contact between a stimulation device and the tongue may be used to detect the shape or outline of a person's tongue on the rectangular arrays used to map their perceptual ability. This may increase the accuracy of the above-described analysis as stimulus elements which are not in contact with the tongue may result in erroneously low sensitivity and discrimination estimations in some cases.

Actively sensing tongue contact/location may be done in real time in useful applications of the device, such as during transmission of information through the device to the user's tongue. For example, a device developed to stimulate a person's tongue to communicate information to the person may actively sense where the tongue is located on the stimulation array and which stimulation elements are in contact with the tongue. This would ensure that the device does not produce a stimulus that will not be felt by the tongue due to tongue movement, inconsistent placement, or poor contact with the device In one embodiment, the electro-tactile stimulation elements described above may be utilized to electrically measure which electrodes are in contact with the tongue. Sensing the location or contact of the tongue may be accomplished by measuring the impedance across different electrodes of the stimulus array which could then be the same electrodes used to stimulate the tongue, or other electrodes specifically for the purpose. Measuring the capacitance of electrodes may also be used to sense contact/location of the tongue. In other implementations, other sensors, such as optical sensors, pressure sensors, thermal sensors, and the like, may be included on the body of the tongue stimulation device that may provide some indication of contact with the user's tongue. The sensors may provide a detected presence of the user's tongue on the body back to the control system, which may then be used to aid in activating the stimulation elements of the tongue stimulation device, as well as in generating the tongue stimulation map for the user described above.

In addition, the tongue stimulation device may be used along with a device to measure an action potential or brain activity originating from stimulation of some part of the tongue. The measurement of the brain activity may be utilized as a substitute or supplement to the feedback received from the subject during the testing. For example, upon application of one or more stimulus to the subject's tongue, brain activity of the subject may be measured through a traditional electroencephalogram (EEG) device, or other methods of measuring brain activity (magnetic resonance imagining (MRI), infrared, etc.). The measured brain activity may then be used as feedback of the subject in response to the applied stimulus. As such, the subject may not need to provide verbal or other feedback in response to the stimulus to indicate the perception of stimulus on the tongue. This method could be used to perform the perceptual mapping techniques described above without eliciting a response from the subject of the tongue mapping procedure.

Further still, the tongue stimulation device may stimulate one part of the tongue with an electrode or other stimulus element and measure the electrical potential of surrounding or nearby electrodes to identify the direction of an action potential resulting from the stimulation of a nerve fiber. Thus, a device may then measure the potential electrically, and possibly with the same electrodes that may be used for stimulating the tongue. By measuring the electrical potential of the nearby electrodes, a general nerve map of the user's tongue may be determined. This information may then be utilized to further enhance the effectiveness of applying stimulus to the subject's tongue. For example, if a nerve path through the subject's tongue is known, the tongue stimulation device may not provide stimulus along the nerve path by more than one electrode. In other words, the stimulus element map for the user may be altered to account for the determined nerve mapping of the user. Other methods of sensing action potential propagation resulting from a stimulus could also be used including infrared, thermal, magnetic, etc. This information obtained from the potential measuring may be included during perceptual mapping of participants to identify the structure and orientation of nerve fibers in the user's tongue.

Through the devices and methods described above, a lingual nerve mapping or perception mapping procedure may be conducted on a user of a tongue stimulation device to map perceived intensity and two-point (or more) discrimination ability for lingual stimulation. The results of the mapping may then be utilized to improve the information provided to the user through the tongue stimulation device by tailoring the delivery of information (i.e., activation of particular stimulus elements) based on a generated map of the user's perceived intensity and two-point discrimination ability.

Embodiments disclosed herein include various operations that are described in this specification. As discussed above, the operations may be performed by hardware components and/or may be embodied in machine-executable instructions, which may be used to cause a general-purpose or special-purpose processor programmed with the instructions to perform the operations. Alternatively, the operations may be performed by a combination of hardware, software, and/or firmware.

The performance of one or more operations described herein may be distributed among one or more processors, not only residing within a single machine, but deployed across a number of machines. In some examples, the one or more processors or processor-implemented modules may be located in a single geographic location (e.g., within a home environment, an office environment, or a server farm). In other embodiments, the one or more processors or processor-implemented modules may be distributed across a number of geographic locations.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores may be arbitrary, and particular operations are illustrated in a context of specific illustrative configurations. In general, structures and functionality presented as separate resources in the examples configurations may be implemented as a combined structure or resource. Similarly, structures and functionality presented as a single resource may be implemented as separate resources.

While the present disclosure has been described with reference to various embodiments, these embodiments are illustrative, and the scope of the disclosure is not limited to such embodiments. Various modifications and additions can be made to the exemplary embodiments discussed herein without departing from the scope of the disclosure. For example, while the embodiments described above refer to particular features, the scope of this disclosure also includes embodiments having different combinations of features, as well as embodiments that do not include all of the described features. Accordingly, the scope of the disclosure is intended to embrace all such alternatives, modifications, and variations, together with all equivalents thereof.

Those skilled in the art will understand and appreciate that various modifications not explicitly described above may be made to the present disclosure and still remain within the scope of the present invention.

Although the present invention has been described with reference to preferred embodiments, persons skilled in the art will recognize that changes may be made in form and detail without departing from the scope of the invention.

What is claimed is:

1. A tongue stimulation device to stimulate a tongue of a user, the device comprising:
    a data storage device storing a stimulation location map unique to a physiology of the tongue of the user of the device;
    a body configured to be placed entirely within a mouth of the user and atop the tongue of the user;
    an array of electro-tactile elements distributed on the body, wherein each of the electro-tactile elements is configured to stimulate an area of the tongue adjacent the electro-tactile element and the stimulation location map comprising an identification of a subset of the array of electro-tactile elements corresponding to a two-point discrimination ability of the tongue of the user of the device;
    a receiver coupled to the body and configured to receive stimulation information that controls activation of the array of electro-tactile elements; and
    at least one processing unit coupled to the body and the receiver and in communication with the data storage device to retrieve the stimulation location map for the user, the at least one processing unit configured to transform the received stimulation information and the stimulation location map into an activation signal for a plurality of electro-tactile elements of the subset of the array of electro-tactile elements and to provide the activation signals to the plurality of electro-tactile elements of the subset of the array of electro-tactile elements causing the stimulation of the area of the tongue based on the stimulation information and the stimulation location map.

2. The tongue stimulation device of claim 1, further comprising:
    an array of thermal elements distributed on the body, wherein each of the thermal elements is configured to heat or cool an area of the tongue adjacent the thermal element;
    wherein the at least one processing unit is further configured to transform the received stimulation information and the stimulation location map for the user into an activation signal for each of the thermal elements.

3. The tongue stimulation device of claim 1, further comprising:
    an array of chemical-producing elements distributed on the body, wherein each of the chemical-producing elements is configured to apply a chemical to an area of the tongue adjacent the chemical-producing element;
    wherein the at least one processing unit is further configured to transform the received stimulation information and the stimulation location map for the user into an activation signal for each of the chemical-producing elements.

4. The tongue stimulation device of claim 1, wherein:
the at least one processing unit comprises a first processing unit; and
the tongue stimulation device further comprises:
a second processing unit configured to be located outside the mouth of the user and to generate the stimulation information; and
a wireless transmitter configured to be located outside the mouth of the user and to transmit the stimulation information wirelessly to the receiver.

5. The tongue stimulation device of claim 1, wherein the stimulation location map for the user further comprises an estimated location of one or more papillae of the user's tongue from an image of the user's tongue.

6. The tongue stimulation device of claim 1, wherein the array of electro-tactile elements distributed on the body comprise a plurality of active electro-tactile elements and a plurality of inactive electro-tactile elements, the plurality of active electro-tactile elements comprising the subset of the array of electro-tactile elements corresponding to the two-point discrimination ability of the tongue of the user of the device identified in the stimulation location map.

7. The tongue stimulation device of claim 1 wherein a physical size of the array of electro-tactile elements corresponds to the two-point discrimination ability of the tongue of the user of the device identified in the stimulation location map.

8. The tongue stimulation device of claim 1, wherein the distribution of the array of electro-tactile elements on the body corresponds to the stimulation location map of the two-point discrimination ability of the tongue of the user of the device.

9. A method for stimulating a tongue of a user, the method comprising:
generating a stimulation location map based on lingual nerve map testing of the tongue of the user, the stimulation location map comprising locations on the tongue of the user corresponding to a two-point discrimination ability of the tongue of the user;
storing the stimulation location map in a data storage device;
receiving, within a mouth of the user, stimulation information;
transforming the received stimulation information and the stimulation map into an identification of a subset of an array of electro-tactile elements configured to stimulate a corresponding area of the tongue and a stimulation signal for a plurality of the subset of the array of electro-tactile elements; and
providing the stimulation signals to the plurality of the subset of the array of electro-tactile elements.

10. The method of claim 9, wherein the array of electro-tactile elements comprise a plurality of active electro-tactile elements and a plurality of inactive electro-tactile elements, the plurality of active electro-tactile elements comprising the subset of the array of electro-tactile elements corresponding to the two-point discrimination ability of the tongue of the user of the device identified in the stimulation location map.

11. The method of claim 9 wherein a physical size of the array of electro-tactile elements corresponds to the two-point discrimination ability of the tongue of the user of the device identified in the stimulation location map.

12. The method of claim 9, wherein lingual nerve map testing of the tongue of the user comprises:
estimating a location of one or more papillae of the user's tongue from an image of the user's tongue.

* * * * *